US008926534B2

(12) United States Patent
McBean et al.

(10) Patent No.: US 8,926,534 B2
(45) Date of Patent: *Jan. 6, 2015

(54) POWERED ORTHOTIC DEVICE AND METHOD OF USING SAME

(75) Inventors: John M. McBean, Boston, MA (US); Kalais N. Narendran, South Burlington, VT (US)

(73) Assignee: Myomo, Inc., Cambridge, MA (US)

( * ) Notice: Subject to any disclaimer, the term of this patent is extended or adjusted under 35 U.S.C. 154(b) by 1353 days.

This patent is subject to a terminal disclaimer.

(21) Appl. No.: 11/857,881

(22) Filed: Sep. 19, 2007

(65) Prior Publication Data

US 2008/0071386 A1 Mar. 20, 2008

Related U.S. Application Data

(60) Provisional application No. 60/826,188, filed on Sep. 19, 2006, provisional application No. 60/889,773, filed on Feb. 14, 2007.

(51) Int. Cl.
*A61H 1/02* (2006.01)
*A61F 5/01* (2006.01)
*A61B 5/11* (2006.01)

(52) U.S. Cl.
CPC .............. *A61F 5/013* (2013.01); *A61F 5/0127* (2013.01); *A61B 5/1116* (2013.01)
USPC ......... 601/5; 601/24; 601/33; 602/16; 602/20

(58) Field of Classification Search
USPC ........ 601/5, 23, 24, 26, 33; 602/5, 16, 18, 20, 602/21
See application file for complete search history.

(56) References Cited

U.S. PATENT DOCUMENTS

| | | | |
|---|---|---|---|
| 3,631,542 A | 1/1972 | Potter | 623/25 |
| 4,030,141 A | 6/1977 | Graupe | 623/25 |

(Continued)

FOREIGN PATENT DOCUMENTS

| | | |
|---|---|---|
| JP | H8687 | 1/1996 |
| JP | 200687533 | 4/2006 |

(Continued)

OTHER PUBLICATIONS

*International Search Report*, International Application No. PCT/US2007/078900 Date of Mailing: May 20, 2008.

(Continued)

*Primary Examiner* — Quang D Thanh
(74) *Attorney, Agent, or Firm* — Sunstein Kann Murphy & Timbers LLP

(57) ABSTRACT

A powered orthotic device includes a brace having a first section and a second section, the first section and the second section operationally coupled at a pivot, the first and the second sections moving about the pivot to define flexion and extension directions, such directions defining inside and outside regions of the brace respectively. The device further includes at least one set of straps that removably attach the first section and the second section to a corresponding limb segment such that the pivot is proximate to a joint between each limb segment. The device also includes and an electromyographic sensor and an actuator assembly in communication with the electromyographic sensor, the actuator assembly mounted to the brace, and occupying a volume of which a majority is disposed proximately to the outside region of the brace, and coupled to the first and second sections of the brace so as to apply a force for driving the first and second sections about the pivot, the force based on signals from the electromyographic sensor.

44 Claims, 27 Drawing Sheets

(56) References Cited

U.S. PATENT DOCUMENTS

| | | | | |
|---|---|---|---|---|
| 4,209,860 | A | | 7/1980 | Graupe ............................ 623/25 |
| 4,650,492 | A | | 3/1987 | Barkhordar et al. ............ 623/24 |
| 4,685,925 | A | | 8/1987 | Childress et al. ............... 623/25 |
| 5,112,296 | A | | 5/1992 | Beard et al. ..................... 602/28 |
| 5,282,460 | A | * | 2/1994 | Boldt ................................. 601/5 |
| 5,466,213 | A | | 11/1995 | Hogan et al. .................... 601/33 |
| 5,682,327 | A | * | 10/1997 | Telepko ........................... 601/34 |
| 5,685,830 | A | | 11/1997 | Bonutti ............................ 602/16 |
| 5,800,561 | A | | 9/1998 | Rodriguez ....................... 623/26 |
| 5,853,005 | A | | 12/1998 | Scanlon ........................... 600/25 |
| 5,888,212 | A | | 3/1999 | Petrofsky et al. ............... 623/24 |
| 5,888,213 | A | | 3/1999 | Sears et al. ...................... 625/24 |
| 5,951,499 | A | * | 9/1999 | Saringer et al. ................. 601/33 |
| 5,954,621 | A | | 9/1999 | Joutras et al. ................. 482/114 |
| 5,980,435 | A | | 11/1999 | Joutras et al. ................. 482/114 |
| RE37,209 | E | | 6/2001 | Hensley et al. ................. 602/26 |
| 6,379,393 | B1 | | 4/2002 | Mavroidis et al. .............. 623/25 |
| 6,532,383 | B2 | | 3/2003 | Maloney et al. .............. 600/546 |
| 6,599,255 | B2 | * | 7/2003 | Zhang ........................... 600/587 |
| 6,616,579 | B1 | | 9/2003 | Reinbold et al. ................ 482/91 |
| 6,660,042 | B1 | | 12/2003 | Curcie et al. .................... 623/24 |
| 6,676,612 | B1 | * | 1/2004 | Beny et al. ........................ 601/5 |
| 6,743,187 | B2 | * | 6/2004 | Solomon et al. ................ 601/33 |
| 6,821,259 | B2 | | 11/2004 | Rahman et al. ................. 601/24 |
| 6,880,487 | B2 | | 4/2005 | Reinkensmeyer et al. ... 119/700 |
| 6,944,496 | B2 | | 9/2005 | Jeong et al. ................... 600/546 |
| 6,966,882 | B2 | | 11/2005 | Horst ................................. 601/5 |
| 6,969,365 | B2 | | 11/2005 | Scorvo ............................ 602/16 |
| 7,182,738 | B2 | * | 2/2007 | Bonutti et al. .................... 601/5 |
| 8,246,559 | B2 | | 8/2012 | Hoffman et al. |
| 2002/0169402 | A1 | | 11/2002 | Hatton et al. ................... 602/16 |
| 2003/0023195 | A1 | | 1/2003 | Rahman et al. ................. 601/24 |
| 2003/0064869 | A1 | | 4/2003 | Reinkensmeyer et al. ....... 482/8 |
| 2003/0120183 | A1 | * | 6/2003 | Simmons ....................... 600/595 |
| 2004/0106881 | A1 | | 6/2004 | McBean et al. ................... 601/5 |
| 2005/0006980 | A1 | | 1/2005 | Horst ............................. 310/309 |
| 2006/0004307 | A1 | | 1/2006 | Horst ................................. 601/5 |
| 2006/0052731 | A1 | | 3/2006 | Shimada et al. |
| 2006/0130594 | A1 | | 6/2006 | Ikeuchi |
| 2007/0191743 | A1 | | 8/2007 | McBean et al. ................... 601/5 |
| 2008/0139968 | A1 | | 6/2008 | Endo et al. |
| 2008/0161937 | A1 | | 7/2008 | Sankai |

FOREIGN PATENT DOCUMENTS

| | | |
|---|---|---|
| JP | 2006167313 | 6/2006 |
| WO | 2004107085 | 12/2004 |
| WO | 2006064657 A1 | 6/2006 |

OTHER PUBLICATIONS

*Written Opinion of the International Searching Authority*, International Application No. PCT/US2007/078900 Date of Mailing: May 20, 2008.

Abul-Haj, et al., "Functional Assessment of Control Systems for Cybernetic Elbow Prostheses—Part II: Application of the Technique", 1990, IEEE Transactions on Biomedical Engineering, vol. 37, No. 11, pp. 1037-1047.

Benjuya, et al., "Hybrid Arm Orthosis", 1990, American Academy of Orthotics and Prosthetics, Journal of Prosthetics & Orthotics, vol. 2, No. 2, pp. 155-163.

Bowen, et al., "Surface EMG and Motor Control of the Upper Extremity in Muscular Dystrophy: A Pilot Study", 2002, IEEE Bioengineering Conf., pp. 289-290.

Brown, et al., "The Exoskeleton Glove for Control of Paralyzed Hands", 1993, IEEE, 1050-4729/93, pp. 642-647.

Downes, et al., "Distributed Control of an Electrically Powered Hip Orthosis", 1994, IEE Control Conference, pp. 24-30.

Fukuda, et al., "EMG-Based Human-Robot Interface for Rehabilitation Aid", Proceedings of the 1998 IEEE International Conference on Robotics and Automation, pp. 3492-3497.

Harwin, et al., "A Review of Design Issues in Rehabilitation Robotics with Reference to North American Research", IEEE Transactions on Rehabilitation Engineering, vol. 3, No. 1, Mar. 1995, 1063-6528/95, pp. 3-13.

Harwin, et al., "Criteria for Interfacing and Control of a Powered Upper Extremity Orthosis", RERC on Rehabilitation Robotics Applied Science and Engineering Laboratories, University of Delaware/A.I. DuPont Institute, Rehabilitation R&D Progress reports, 1995, vol. 33, p. 215.

Homma, et al., "An Upper Limb Motion Assist System, Experiments with Arm Models", Proceedings of the 1996 IEEE/RSJ Int'l Conference on Intelligent Robots and Systems, Victoria, B.C., Canada, Oct. 1998, 0-7803-4465-0/98, pp. 758-763.

Johnson, et al., "Development of a Mobility Assist for the Paralyzed, Amputee, and Spastic Patient", 1996, IEEE; 0-7803-3131-1/96; pp. 67-70.

Kawamoto, et al., "Comfortable Power Assist Control Method for Walking Aid by HAL-3", 2000, IEEE SMC, TP1B2; 6 sheets.

Kawamura, et al., "A Design of Motion-Support Robots for Human Arms using Hexahedron Rubber Actuators", 1997, IROS, IEEE, pp. 1520-1526.

Kazerooni, "Stability and Performance of Robotic Systems Worn by Humans", University of Minnesota, Mechanical Engineering Dept., May 13-18, 1990 IEEE, vol. 1, pp. 558-563.

Kiguchi, et al., "An Exoskeletal Robot for Human Elbow Motion Support-Sensor Fusion, Adaptation, and Control", 2001, IEEE Transactions on Systems, Man, and Cybernetics-Part B; Cybernetics, vol. 31, No. 3, Jun. 2001, 1083-4419/01, pp. 353-361.

Kiguchi, et al., "An Exoskeleton System for Elbow Joint Motion Rehabilitation", Proceedings of the 2003 IEEE/ASME International Conference on Advanced Intelligent Mechatronics (AIM 2003), pp. 1228-1233.

Krebbs, et al., "Robot-Aided Neurorehabilitation in Stroke: Three-Year Follow-Up", 1999, Int'l Conference on Rehabilitation Robotics, pp. 34-41.

Krebs, et al., "Increasing Productivity and Quality of Care: Robot-Aided Neuro-Rehabilitation", Journal of Rehabilitation Research and Development, vol. 37, No. 6, Nov./Dec. 2000, pp. 1-4.

Krebs, et al., Robot-Aided Neurorehabilitation, 1998, IEEE Transactions on Rehabilitation Engineering vol. 6, No. 1, Mar. 1998, pp. 75-77.

Lee, et al., Power Assist Control for Walking Aid with HAL-3 Based on EMG and Impedance Adjustment around Knee Joint, 2002, IEEE/RSJ Int'l Conf. on Intelligent Robots and Systems, EPFL, Lausanne, Switzerland, Oct. 2002; 2002 IEEE; 0-7803-7396-7.02 pp. 1499-1504.

Lee, et al., "A New Exoskeleton-type Masterarm with Force Reflection: Controller and Integration", 1999, IEEE/RSJ International Conference on Intelligent Robots and Systems, pp. 1438-1443.

Lum, et al., "A Robotic System for Upper-Limb Exercises to Promote Recovery of Motor Function Following Stroke", ICORR '99: International Conference on Rehabilitation Robitics, Stanford, CA, pp. 235-239.

Lum, et al., "Quantification of Force Abnormalities During Passive and Active-Assisted Upper-Limb Reaching Movements in Post-Stroke Hemiparesis", 1999, IEEE Trans on Biomed, vol. 46, No. 6, pp. 652-662.

Lum, et al., "Robotic Assist Devices for Bimanual Physical Therapy: Preliminary Experiments", 1993, IEEE Transactions on Rehabilitation Engineering, vol. 1, No. 3, pp. 185-191.

Morita, et al., "Basic Study on Rehabilitation Support System for Upper Limb Motor Function", 2002, IEEE AMC, pp. 127-132.

Parsons, et al., An Adaptable User Interface and Controller for a Rehabilitation Robotoc Arm, 1997, ICAR, pp. 919-923.

Popovic, et al., "Hybrid Assistance System—The Motor Neuroprosthesis", 1989, IEEE Transactions on Biomedical Engineering, vol. 36, No. 7, pp. 729-737.

Rabischong, et al., "Control and Command of a Six Degrees of Freedom Active Electrical Orthosis for Paraplegic Patent", 1990, IEEE International Workshop on Intelligent Robots and Systems, pp. 987-991.

Reinkensmeyer, et al., "Guidance-Based Quantification of Arm Impairment Following Brain Injury: A Pilot Study", 1999, IEEE Transactions on Rehabilitation Engineering, vol. 7, No. 1, pp. 1-11.

(56) References Cited

OTHER PUBLICATIONS

Romilly, et al. "A Functional Task Analysis and Motion Stimulation for the Development of a Powered Upper-Limb Orthosis", 1994, IEEE Transactions on Rehabilitation Engineering, vol. 2, No. 3, pp. 119-129.

Rosen, et al., "A Myosignal-Based Powered Exoskeleton System", 2001, IEEE Transactions on System, Man, and Cybernetics, Part A: Systems and Humans, vol. 31, No. 3, pp. 210-222.

Seliktar, et al., "Evaluation of Functional Capabilities of People with Muscular Dystrophy as Potential Users of Powered Orthoses", ASME Summer Bioengineering Conference, Jun. 16-20, 1999, Blue Sky Montana, 2 sheets.

Timoszyk, et al., "Robot-Assisted Locomotion Training after Spinal Cord Injury: Comparison of Rodent Stepping in Virtual and Physical Treadmill Environments", Department of Mechanical and Aerospace Engineering and Center for Biomedical Engineering, University of California, Irvine, 1990 IEEE International Conference, pp. 1-14.

Triolo, et al., "The Theoretical Development of a Multichannel Time-Series Myoprocessor for Simultaneous Limb Function Detection and Muscle Force Estimation", 1989, IEEE Transactions on Biomedical Engineering, vol. 36, No. 10, pp. 1004-1017.

Umetani, et al., "Skil Mate", Wearable Exoskeleton Robot, 1999, IEEE, 0-7803-5131, pp. IV984 to IV988.

Wiegner, Allen W., et al., "Design of a Triceps Orthosis for C5/C6 Quadriplegics" 0-7803-0785, 2/92, IEEE, pp. 1485-1486.

Wu, et al., "A Study of Neuromuscular-like Control in Rehabilitation Robot", Proceedings of the 1996 IEEE International Conference on Rotobics and Automation, Minneapolis, MN, 0-7803-2988-4/96, Apr. 1996, pp. 1178-1183.

Zardoshti-Kermani, et al., "EMG Feature Evaluation for Movement Control of Upper Extremity Prostheses", 1995, IEEE Transactions on Rehabilitation Engineering, vol. 3, No. 4, pp. 324-333.

Benjuya et al., "Myoelectric Hand Orthosis," Journal of Prosthetics and Orthotics, vol. 2, No. 2, pp. 149-152, 1990.

Shibata et al., "A Study on Self-Powered Ankle Foot Orthosis," Japan Society of Mechanical Engineering, No. 06-7, Dynamics and Design Conference 2006, Aug. 6-9, 2006.

* cited by examiner

CO=Command Output to actuation system
$OS_i$ =Output Signal (from particular relationship. Example: $OS_{EMGI}$).

① $CO = A(OS_{EMGI}) + B \cdot (OS_{position}) - C \cdot (OS_{elapsed\ time})$;

where A, B, C are constants.

② $CO = S_{in}(OS_{position}) + \dfrac{(OS_{EMGI})^2}{2} - OS_{current}$

③ If $OS_{time} \leq D$, then $CO = E \cdot OS_{EMGI}$

If $OS_{time} > D$, then $CO = E \cdot OS_{EMGI} - F \cdot OS_{time}$;

where D, E, F are constants.

④ If $OS_{EMGI} \leq G$, and $OS_{temp} \leq H$, and $|OS_{position}| \leq I$, then $CO = OS_{EMGI}$ ELSE, CO = ∅;
where G, H, I are constants.

FIG. 20

OS $_{position}$ = Output Signal (position) (From Figure 25)
OS $_{temperature}$ = Output Signal (temperature) (From Figure 26)
OS $_{EMGI}$ = Output Signal (EMGI) (From Figure 24)

If OS $_{position}$ ≤ E and OS $_{temperature}$ ≤ G,
    then CO = OS $_{EMGI}$
ELSE CO=0

US 8,926,534 B2

POWERED ORTHOTIC DEVICE AND METHOD OF USING SAME

CROSS-REFERENCE TO RELATED APPLICATIONS

This patent application claims priority to U.S. Provisional Patent Application No. 60/826,188 filed Sep. 19, 2006 and U.S. Provisional Patent Application No. 60/889,773 filed Feb. 14, 2007, the disclosures of which are incorporated by reference herein in their entirety.

FIELD OF THE INVENTION

The invention generally relates to orthotic devices and, more particularly, the invention relates to powered orthotic devices and methods of using same for rehabilitation or functional aids.

BACKGROUND OF THE INVENTION

Stroke, brain injury, and other neuromuscular trauma survivors are often left with hemipareisis, or severe weakness in certain parts of the body. The result can be impaired or lost function in one or more limbs. It has been shown that people can rehabilitate significantly from many of the impairments following such neurological traumas. Further, it has been shown that rehabilitation is much more effective, and motor patterns re-learned more quickly, if the rehabilitative exercise regime includes the execution of familiar and functional tasks. Following neuromuscular trauma, however, the control or strength in the afflicted limb or limbs may be so severely diminished that the patient may have difficulty (or be unable) performing constructive, functional rehabilitation exercises without assistance.

SUMMARY OF THE INVENTION

In accordance with one embodiment of the invention, a powered orthotic device includes a brace having a first section and a second section, the first section and the second section operationally coupled at a pivot, the first and the second sections moving about the pivot to define flexion and extension directions, such directions defining inside and outside regions of the brace respectively. The device further includes at least one set of straps that removably attach the first section and the second section to a corresponding limb segment such that the pivot is proximate to a joint between each limb segment. The device further includes an electromyographic sensor and an actuator assembly in communication with the electromyographic sensor, the actuator assembly mounted to the brace, and occupying a volume of which a majority is disposed proximately to the outside region of the brace, and coupled to the first and the second sections of the brace so as to apply a force for driving the first and second sections about the pivot, the force based on signals from the electromyographic sensor.

In accordance with related embodiments, the actuator assembly may include a motor and the motor may be disposed proximately to the outside region of the brace. The actuator assembly may include a motor in a housing and a drive arrangement coupled to the motor, the housing may be disposed proximate to the pivot and coupled to the brace. The housing may have a longitudinal axis that is parallel to an axis of rotation of the joint or that is perpendicular to an axis of rotation of the joint. The device may further include a control system in communication with the electromyographic sensor and with the motor for controlling operating parameters of the device. The control system may be in communication with the electromyographic sensor and the motor via a cable. The control system may be in communication with the electromyographic sensor and the motor through a wireless system. The control system may include a user interface through which a user interacts with the device. The control system may include a processing system for receiving the signals from the electromyographic sensor and generating output signals to the motor. The processing system may include software for limiting a range of motion of the sections about the joint. The control system may include a data management system for storing data received from the device and/or from a user.

The device may further include a user interface, in communication with the electromyographic sensor and the motor, through which a user interacts with the device. The device may further include a processing system, in communication with the electromyographic sensor and the motor, for receiving the signals from the electromyographic sensor and generating output signals to the motor. The processing system may include a data management system for storing data received from the device and/or from a user. The device may further include motion limits coupled to the drive assembly for limiting a range of motion of the sections about the joint. The motion limits may be provided by mechanical stops and/or by sensors. The device may further include a planetary gear head coupled to the motor and to the drive assembly. The drive assembly may include a chain and sprocket. The brace may include at least one pad coupled to the first section, the second section, the pivot, or a combination thereof. The brace may be removably attached to an arm and the pivot may be proximate to an elbow. The brace may be removably attached to an arm and a hand and the pivot may be proximate to a wrist. The brace may be removably attached to a hand and at least one finger and the pivot may be proximate to a finger joint. The electromyographic sensor may be coupled to at least one of the straps, to at least one of the sections, or both.

In accordance with another embodiment of the invention, a powered orthotic device includes a brace having a first section and a second section, the first section and the second section operationally coupled at a pivot, the first and the second sections moving about the pivot to define flexion and extension directions, such directions defining inside and outside regions of the brace respectively. The device further includes at least one set of straps that removably attach the first section and the second section to a corresponding limb segment such that the pivot is proximate to a joint between each limb segment. The device further includes an electromyographic sensor and an actuator assembly in communication with the electromyographic sensor, the actuator assembly mounted to the brace and coupled to the first and the second sections of the brace so as to apply a force for driving the first and second sections about the pivot, the force based on signals from the electromyographic sensor. The device further includes a controller coupled to the actuator assembly that controls operation of the actuator assembly and a user interface, coupled to the controller, that permits user adjustment of force parameters of the actuator assembly.

In accordance with related embodiments, the user interface may permit separate user adjustment of assistance levels in the flexion direction and the extension direction independently of one another.

In accordance with another embodiment of the invention, a powered orthotic device includes a brace having a first section and a second section, the first section and the second section operationally coupled at a pivot, the first and the second sections moving about the pivot to define flexion and extension directions, such directions defining inside and outside regions of the brace respectively. The device further includes at least one set of straps that removably attach the first section and the second section to a corresponding limb segment such that the pivot is proximate to a joint between each limb segment. The device further includes an electromyographic sensor and an actuator assembly in communication with the electromyographic sensor, the actuator assembly mounted to the brace and coupled to the first and the second sections of the brace so as to apply a force for driving the first and second sections about the pivot, the force based on signals from the electromyographic sensor. The device further includes a controller coupled to the actuator assembly that controls operation of the actuator assembly and a user interface, coupled to the controller, that permits user selection of operational mode of the device from among at least two of high assist, low assist, resistive, therapeutic training, and functional assistive.

In accordance with related embodiments, the user interface may permit a user selection of operational mode from among at least three of high assist, low assist, resistive, therapeutic training, and functional assistive.

In accordance with another embodiment of the invention, a method of providing therapeutic training to a subject experiencing compromised functionality in moving a limb about a joint includes using an EMG-controlled orthotic device to restore at least partial functionality in moving the limb about the joint, and in the course of using the orthotic device, having the subject perform a series of physical tasks requiring at least one of motion of the limb about the joint or locking of the limb in a fixed position relative to the joint.

In accordance with related embodiments, using the orthotic device may include providing feedback while the subject performs a physical task or the series of physical tasks. Providing feedback may include providing visual feedback of an EMG signal on a control screen while the subject performs the physical task or the series of physical tasks. Using the orthotic device may include providing an adjustment of level of assistance from the orthotic device. Using the orthotic device may include providing at least two levels of assistance during a physical task or the series of physical tasks, the two levels may including a first level of assistance and an increased level of assistance relative to the first level of assistance or may include a first level of assistance and a decreased level of assistance relative to the first level of assistance.

In accordance with another embodiment of the invention, a method of providing therapeutic training to a subject experiencing compromised functionality in moving a limb about a joint includes determining an unassisted level of the subject's functionality in moving the limb about the joint, using an EMG-controlled orthotic device to restore at least partial functionality in moving the limb about the joint, and in the course of using the orthotic device, having the subject perform a series of physical tasks associated with a new level of functionality higher than the unassisted level, so that the subject experiences movement patterns associated with the new level.

In accordance with related embodiments, using the orthotic device may include providing feedback while the subject performs a physical task or the series of physical tasks. Providing feedback may include providing visual feedback of an EMG signal on a control screen while the subject performs the physical task or the series of physical tasks. Using the orthotic device may include providing an adjustment of level of assistance from the orthotic device. Using the orthotic device may include providing at least two levels of assistance during a physical task or the series of physical tasks, the two levels may including a first level of assistance and an increased level of assistance relative to the first level of assistance or may include a first level of assistance and a decreased level of assistance relative to the first level of assistance.

BRIEF DESCRIPTION OF THE DRAWINGS

The foregoing features of the invention will be more readily understood by reference to the following detailed description, taken with reference to the accompanying drawings, in which:

FIG. 20 shows an illustrative control algorithm according to illustrative embodiments of the present invention;

DESCRIPTION OF ILLUSTRATIVE EMBODIMENTS

Figure 1:
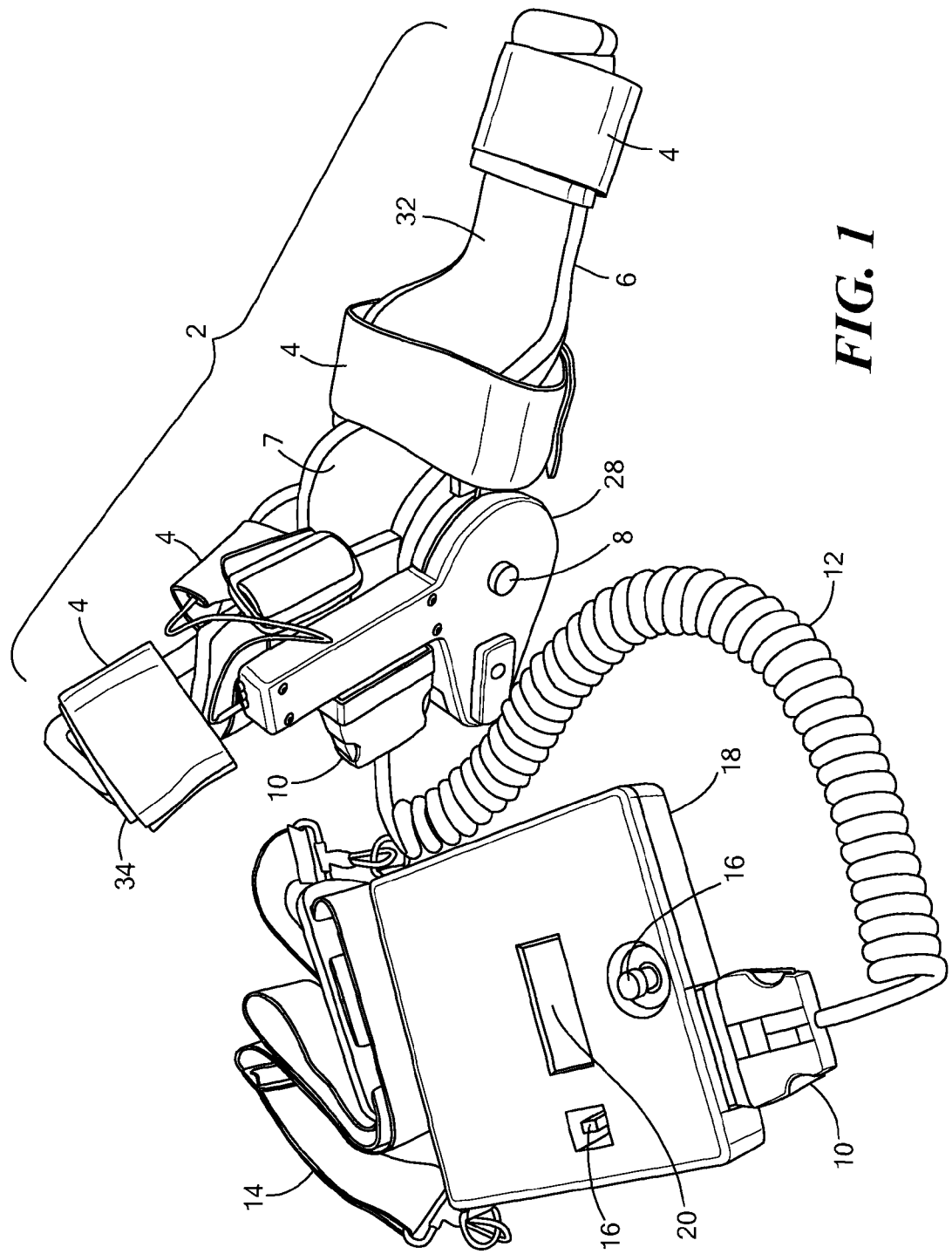
FIG. 1 shows a powered orthotic device according to illustrative embodiments of the present invention.

Definitions. As used in this description and the accompanying claims, the following terms shall have the meanings indicated, unless the context otherwise requires:

An "orthotic device" is a support or brace for weak or ineffective joints or muscles. An orthotic device is worn over existing body parts.

An "EMG-controlled" orthotic device is an orthotic device that is designed to cause the application of force to a body part with respect to a joint, at least under some conditions in response to a sensed EMG signal, so as to assist in causing motion of the body part relative to the joint. An "EMG-controlled" orthotic device includes, but is not limited to, a device (called herein an "asymmetric EMG-controlled device") that provides (i) in response to a first sensed EMG signal, a first force in a first direction and (ii) in response to one or more conditions selected from the group consisting of (a) absence of any sensed EMG signal, (b) the first sensed EMG signal, and (c) a second sensed EMG signal, a second force in a second direction that is opposed to the first direction, wherein the first force as a function of the first sensed EMG signal is asymmetric in relation to the second force in the second direction.

A "prosthesis" is an artificial device to replace a missing part of the body.

A "rehabilitation aid" is a device or treatment whose purpose is to restore function in a weak, damaged, or unhealthy body part. The purpose of a rehabilitation aid is to assist in the return of function to the body part itself, rather than compensating for or replacing that body part.

A "functional aid" is a device that serves to enhance a user's functional capacity. A functional aid does not necessarily provide rehabilitative benefit to the user, rather it serves as an assistive tool whose benefits are only realized while the tool is being used.

Embodiments of the present invention provide a portable, wearable powered orthotic device and method of using same which enhances the wearer's functional capacity while it is being worn. Embodiments of the device may be used as a rehabilitation aid or a functional aid to enhance the user's functional capacity so that he or she may be able to perform the tasks and exercises that will promote further motor pattern re-learning and rehabilitation. The device is worn by the user and may apply assistive torques and forces to the user's body according to the intended motion of the user, as measured and processed by the device. As such, the device assists the user in achieving the motion patterns that he or she initiates and controls.

Often in certain neuromuscular conditions, such as stroke, a person is capable of only asymmetric control of a particular joint. For example, the person may have the ability to flex or extend the joint, but may not be able to perform both functions. In this case, the muscle group that controls flexion about the joint may be controllable by the user and its activity may be readable with the appropriate sensors, while the user's ability to control the muscle group responsible for extension about the joint may be impaired. Similarly, the opposite may be true, e.g., the user has control in the extension direction, but not the flexion direction.

Cases of asymmetric control, such as the one described above, may necessitate a device with a corresponding asymmetric control algorithm that may be controlled by the user, offering enhanced functional performance and motor pattern reinforcement to help with rehabilitation and retraining. For the purposes of rehabilitation and motor pattern relearning, the motion of the device should accurately represent the user's intent, so that the device can re-teach and reinforce naturally learned motor patterns. For example, part of a reaching task involves relaxing the flexors (biceps, brachioradialis) and learning to let the tension in the extensors (triceps) dominate and extend the arm. Such a task would clearly be difficult for a person with an inability to apply tension with his or her triceps. The proposed control algorithm achieves and reinforces a natural reaching pattern for such a person by applying a torque that mimics the torque applied by the extensors, based solely on the relaxation state of the flexors, and in some cases other non-muscular sensory inputs.

Embodiments of the present invention may use an asymmetric control algorithm that mimics, in real time, the natural patterns of motion and force about a joint, even in the absence of the user's ability to control one of the major muscle groups (flexors or extensors) that control force and motion about the joint. Without measuring, interpreting, or processing a signal as an indicator of user intent in the second direction (the compromised direction—either flexion or extension), the device may apply torque in real-time that is directly based on the EMG signals of only the muscle group that controls motion in the first direction (the uncompromised direction). The details of this asymmetric control algorithm are described in more detail below.

FIG. 1 shows a powered orthotic device according to an embodiment of the present invention. The device includes a wearable component 2 secured to a limb or body part, the wearable component 2 in communication with a control system 18 which may be used to set or control some of the parameters of the device. Connection to the control system 18 may be via a flexible, compliant cable 12, as shown, so as to minimize impact on the mobility of the user. The cable 12 may have quick disconnect cable connectors 10 at its ends, so that it may be quickly and easily connected or disconnected from the wearable component 2 or the control system 18. This facilitates donning and doffing of the device, as the wearable component 2 may be secured to a limb of the user first, and then the cable 12 may be subsequently connected. Although a cable 12 is shown, the wearable component 2 may be in communication with the control system 18 via other interface devices. For example, the wearable component 2 may be capable of wireless communication (implemented with wireless techniques, e.g., microwave, infrared, radio frequency or other transmission techniques) with the control system 18. The wearable component 2 may also be in communication with other external power supplies, electronics, controllers, actuators, etc., whether located on or in the control system or elsewhere. The control system 18 may be worn or carried by the user or may be remotely located, such as sitting stationary on a table.

Referring also to FIGS. 2-13, the wearable component 2 includes a brace 7 which may have a first section 32 and a second section 34 operatively coupled at a pivot 8. The brace 7 may include more than two sections, and the two or more sections may be disposed parallel to each other or in series with one another. For example, one or more sections may be placed on the fingers and/or along one finger. The wearable component 2 also includes at least one set of straps 4 that removably attach each section 32, 34 to a corresponding limb segment (e.g., the first section 32 to a first limb segment and the second section 34 to a second limb segment) such that the pivot 8 is placed near to a joint between each limb segment and is aligned with the axis of rotation of the joint. For example, with an elbow brace, the first section 32 may be removably attached to the upper arm and the second section 34 may be removably attached to the lower arm. The sections 32, 34 provide coupling to the portions of the limb both above and below the joint, and the straps 4 hold the brace 7 in place around the limb and joint. The straps 4 may be soft, pliable elastic straps or stiffer inelastic straps. Preferably, the straps 4 near the joint or pivot 8 are soft and elastic to protect the skin from abrasion since these straps tend to bunch up when the device is in operation. Similarly, the stiffer, more inelastic straps are preferably used at positions away from the joint to provide rigid coupling and reliable torque application to the limb sections. The straps 4 may be made of a metal, a fabric, a plastic or a combination thereof. In one embodiment, the straps 4 may include one or more webs of material, one or more laces, an adhesive and/or a coupling mechanism that may secure the brace 7 to the user's limb or body part instead of, or in addition to, the straps 4 as shown. For example, the brace 7 may be secured in place with clamps, suction or an enclosure that encircles the user's limb and then is tightened or ratcheted in to place.

Figure 4:
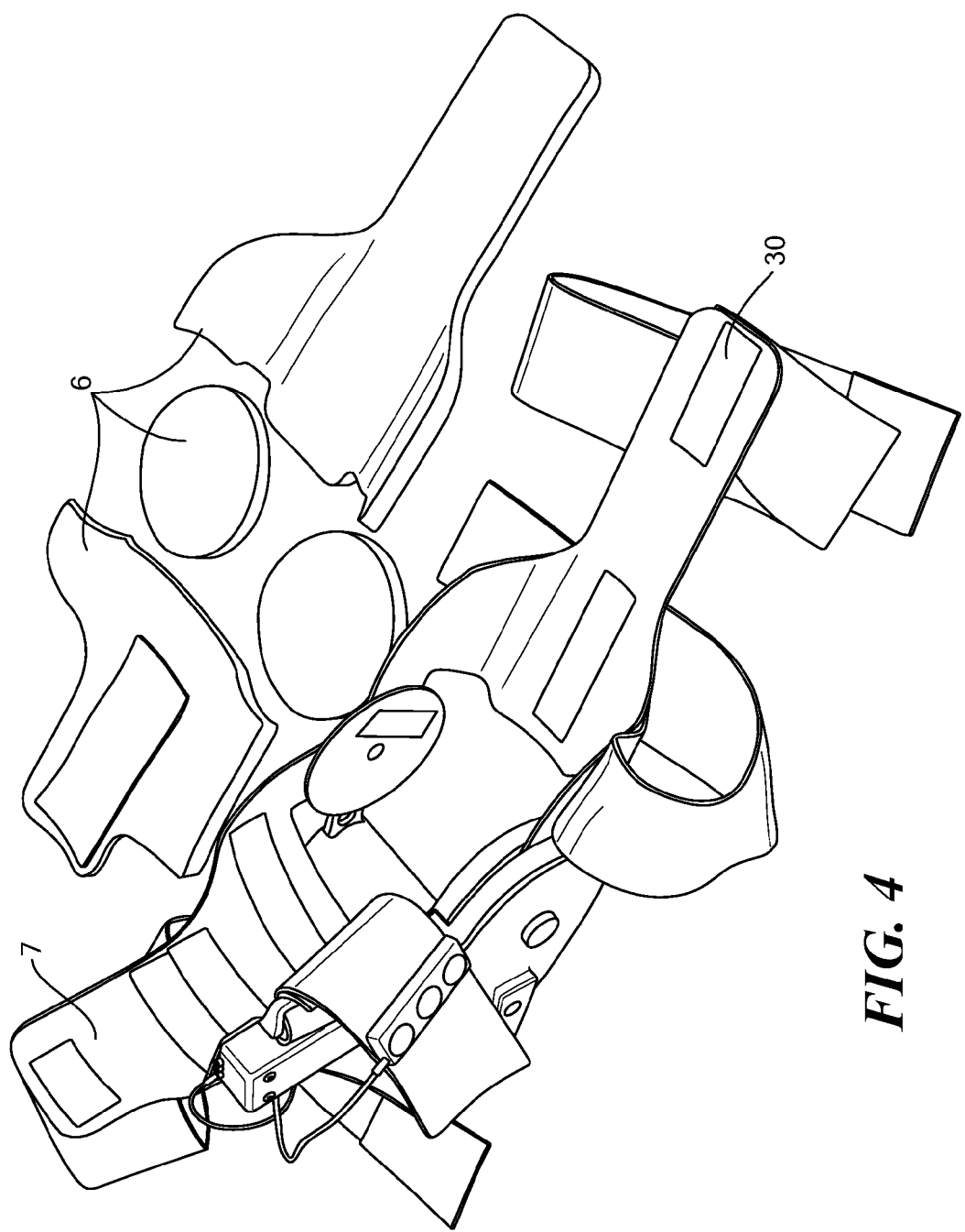
FIG. 4 shows the wearable component with padding removed according to illustrative embodiments of the present invention.
Figure 5:
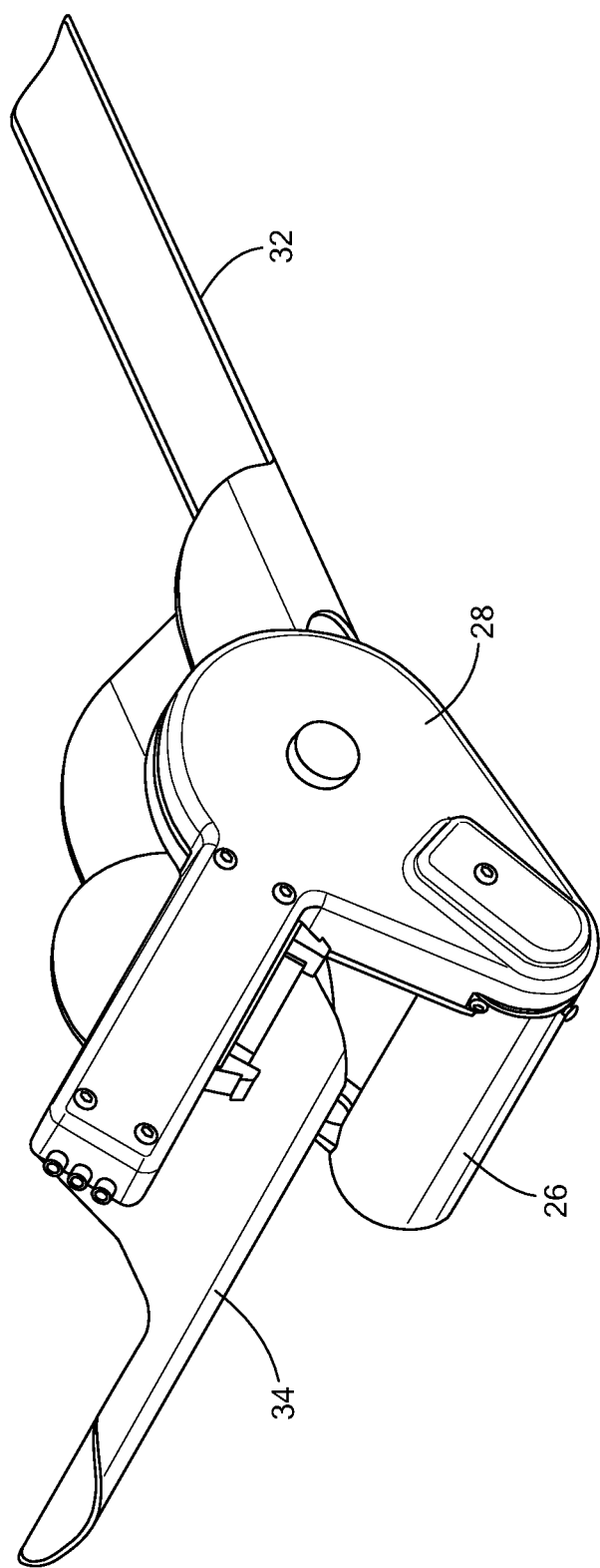
FIG. 5 shows a schematic view of the wearable component according to illustrative embodiments of the present invention.
Figure 6:
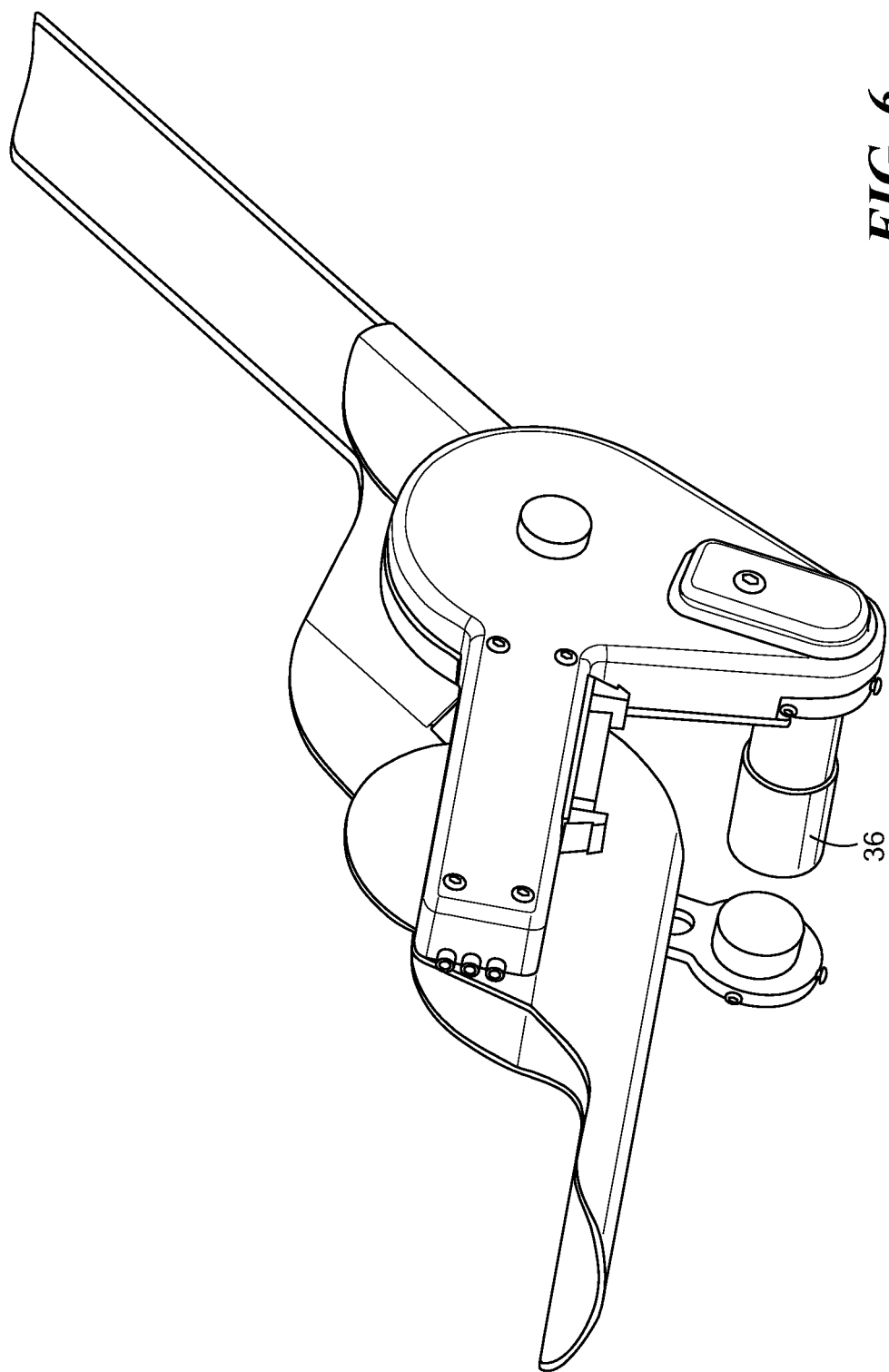
FIG. 6 shows a schematic view of the wearable component with motor housing removed according to illustrative embodiments of the present invention.
Figure 7:
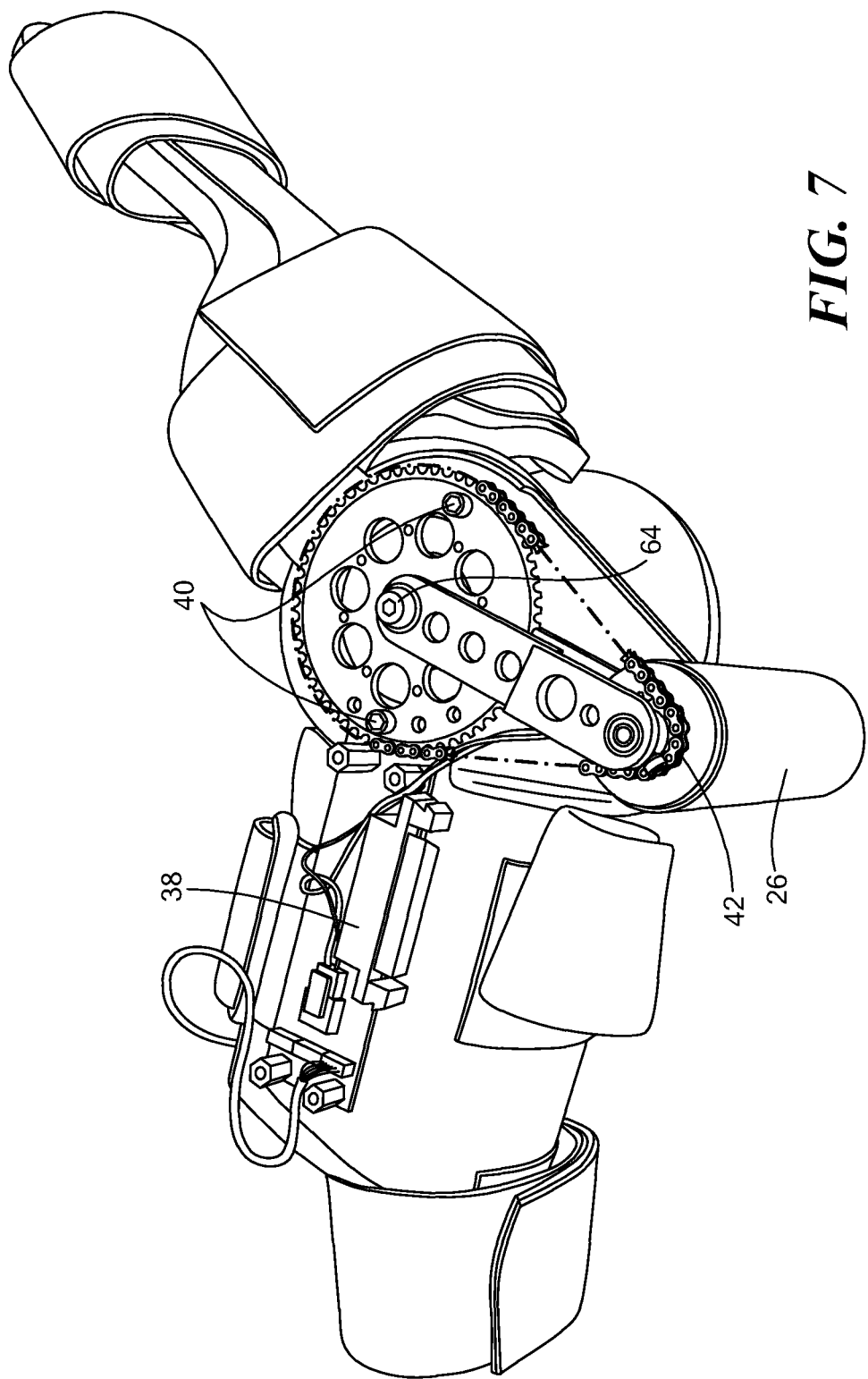
FIG. 7 shows the wearable component with plastic cover removed according to illustrative embodiments of the present invention.

The brace 7 may also include padding 6, which may be removably coupled to the two sections 32, 34 and the pivot 8, as shown in FIG. 4. For example, the padding 6 may be coupled to the sections 32, 34 or the pivot 8 using hook and loop fasteners 30. The padding 6 may be interchangeable and have various thicknesses in order to adjust the size of the brace, e.g., thicker pads may be used to accommodate smaller arms or limbs. The padding 6 may also be removed in order to clean the padding 6 after use of the device.

Figure 2:
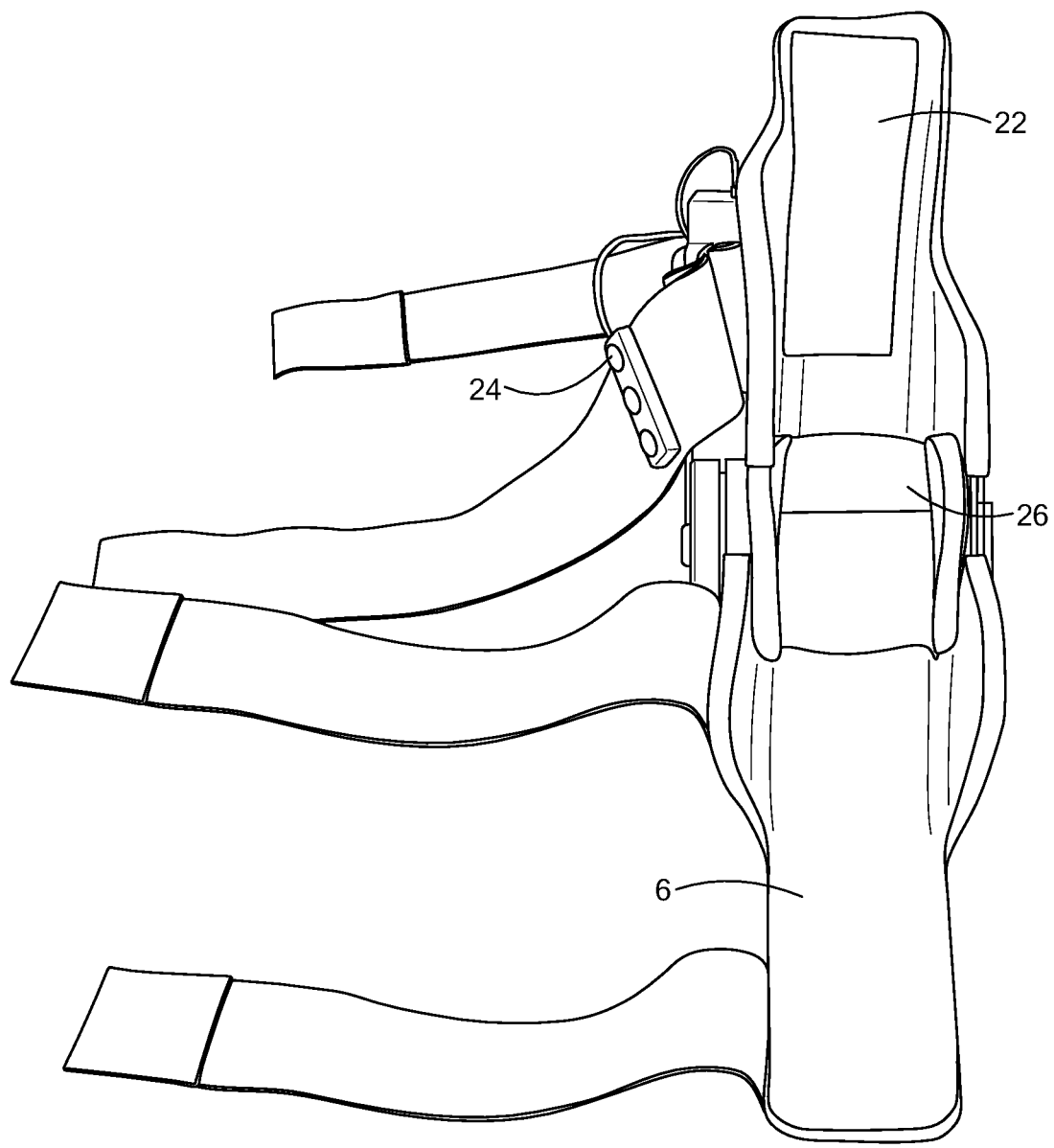
FIG. 2 shows a wearable component of the powered orthotic device for an arm according to illustrative embodiments of the present invention.

The wearable component 2 also includes a sensing system having sensors 24 that measure electromyographical (EMG) signals from a user's muscles. For example, the EMG sensors 24 may be placed in contact with the user's skin and/or may be embedded under the user's skin near to the muscles of interest. The sensing system may also contain sensors in or on both the wearable component 2 and the control system 18. Thus, the sensing system may sense other signals from a user. For example, the sensing system may sense EMG signals from a least one muscle group, and may sense other signals, such as position, velocity, force, torque, time, temperature, current, pulse, blood pressure, etc. In order to assure reliable sensor coupling to the skin, the sensors 24 may be held against the skin in a compliant way. Thus, the electromyographic sensors 24 may be coupled to one or more of the straps 4, as shown in FIG. 2, or may be coupled to one or both of the sections 32, 34. Although EMG sensors are mentioned throughout the application, sensors sensing EEG signals may be used instead of, or in addition to, the EMG sensors 24.

Figure 3:
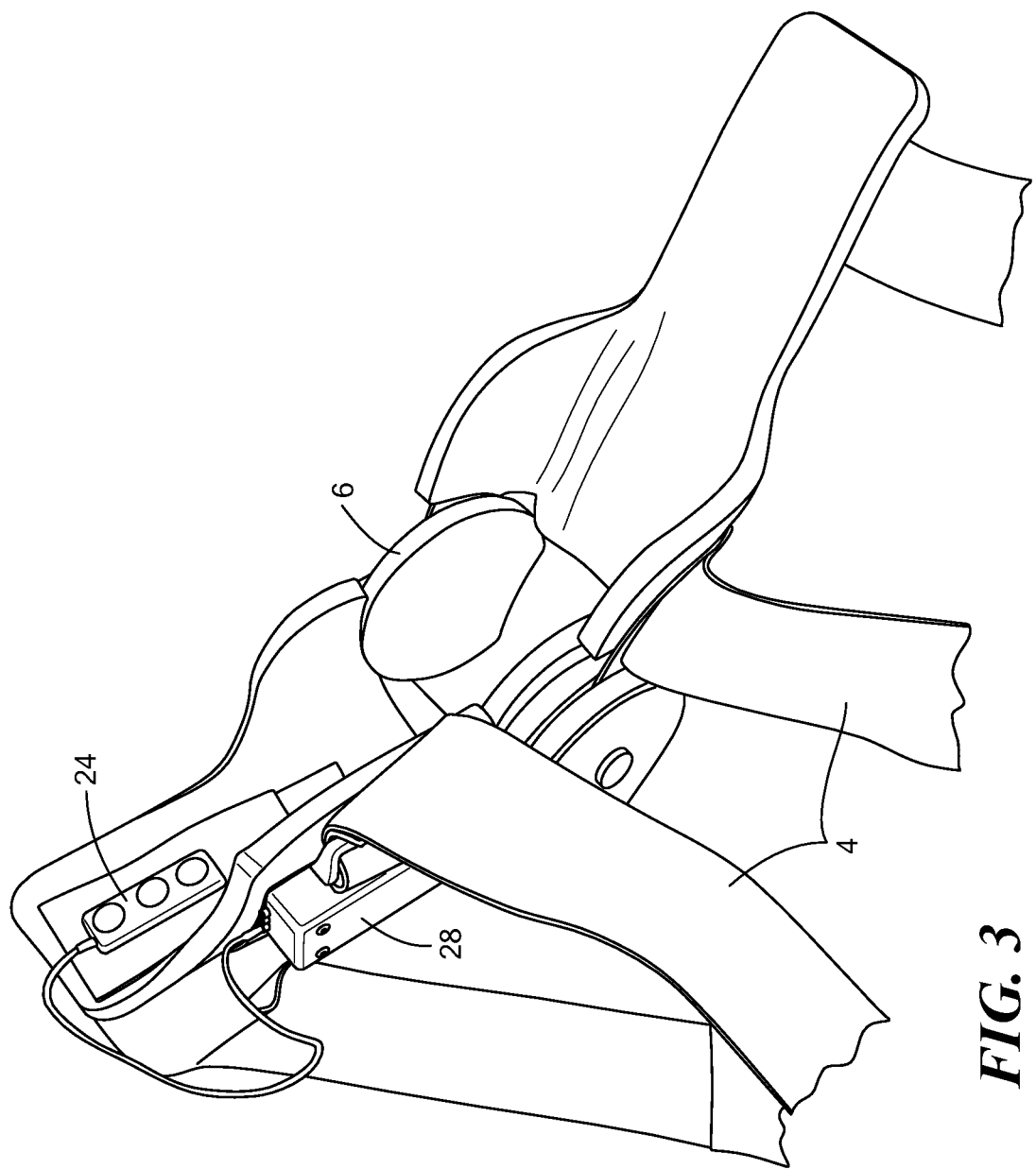
FIG. 3 shows the wearable component with sensors in position according to illustrative embodiments of the present invention.

If the padding 6 is used, then the sensors 24 may be coupled to a compliant padding element 22 coupled to the sections 32, 34, as shown in FIG. 3. Flexible EMG sensors or electrodes 24 may be used to ensure constant contact of the sensors 24 against the user's skin. Compliance, flexibility, and elasticity may be designed into the sensors 24, which may include a sensor housing, such that the sensors 24 may move as the skin moves and not lose contact with the skin's surface. For example, an elastic, compliant spring-like material or structure, e.g., made of metal, plastic, foam, fabric, rubber or any combination thereof, may be applied to the back of the sensors 24. The compliant structure may allow the sensor to be held in place with an inelastic strap, while the inherent compliance and elasticity in the sensor mount enable the sensor to maintain pressure against the skin's surface despite motion and distortion of the surface of the skin, the strap, and/or the brace. Alternatively, or in addition, the sensors 24 may be placed in recessed pockets in the strap 4. The recessions in the strap may enable reliable, repeatable sensor placement, while keeping sensor pressure low but consistent. The sensor strap may be worn under the brace 7, or may be integrated into the brace 7.

As shown in more detail in FIGS. 5-13, the wearable component 2 may further include an actuator assembly for applying torques and forces to the brace 7. The actuator assembly may include a motor and a gearhead 36 in a housing 26, the housing 26 disposed near to the pivot 8 and coupled to the first and second sections 32, 34 of the brace 7. As shown, the housing 26 may be located beneath the user's elbow, providing a protective shell to the motor and gearhead and allowing the wearable component 2 to be place on a table top or hard surface without the elbow contacting the table, thus reducing the risk of pain or injury to the user. The motor may be parallel to and co-axial with an axis of rotation of the joint or may be parallel to, but not co-axial with the axis. Alternatively, the motor may be perpendicular to the axis of rotation of the joint.

The actuator assembly also may include a drive assembly 42, 44 coupled to the motor and gearhead 36 and coupled to the sections 32, 34 of the brace 7 at locations proximate to the pivot 8 so as to apply a force for driving the sections 32, 34 about the pivot 8. The force may be based on the EMG signals from the sensors 24, on preset values or parameters stored in the control system 18, on other inputs, or a combination thereof. Plastic covers 28 may be used to surround the components of the drive assembly 42, 44 to protect the user and others, and also to protect the drive assembly 42, 44 components from foreign objects. Similarly, water proof or resistant, dirt, dust and/or electromagnetic radiation enclosures may be used to surround the electrical and/or mechanical components of the device to protect the device from the environment. The actuator assembly is preferably located in an unobtrusive location to increase wearer comfort and mobility, e.g., on the side of the brace away from the user's body so that it will not abrade the user's body when the device is in use.

Figure 12:
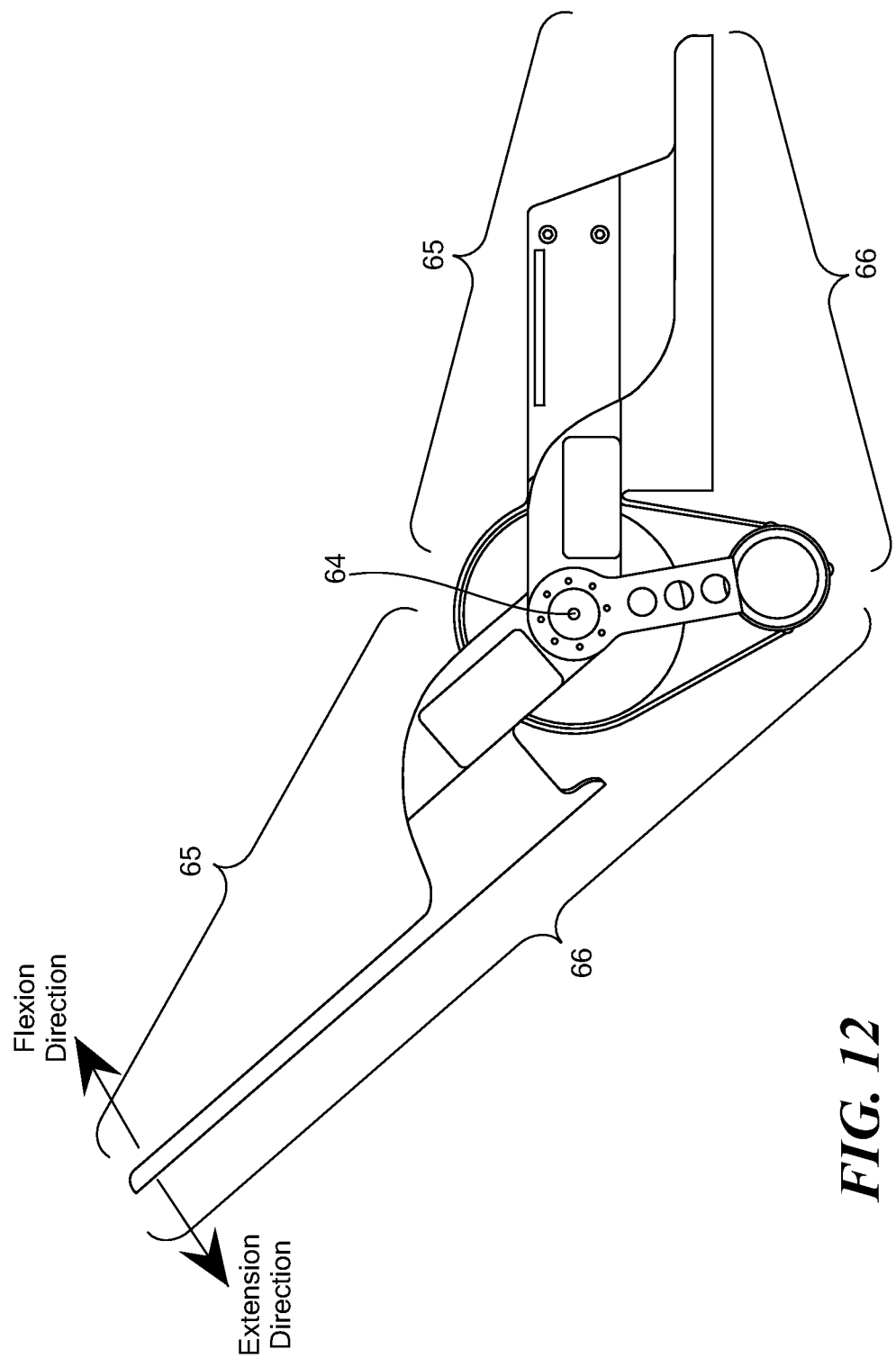
FIG. 12 shows a schematic view of the wearable component with the plastic cover removed according to illustrative embodiments of the present invention.
Figure 13:
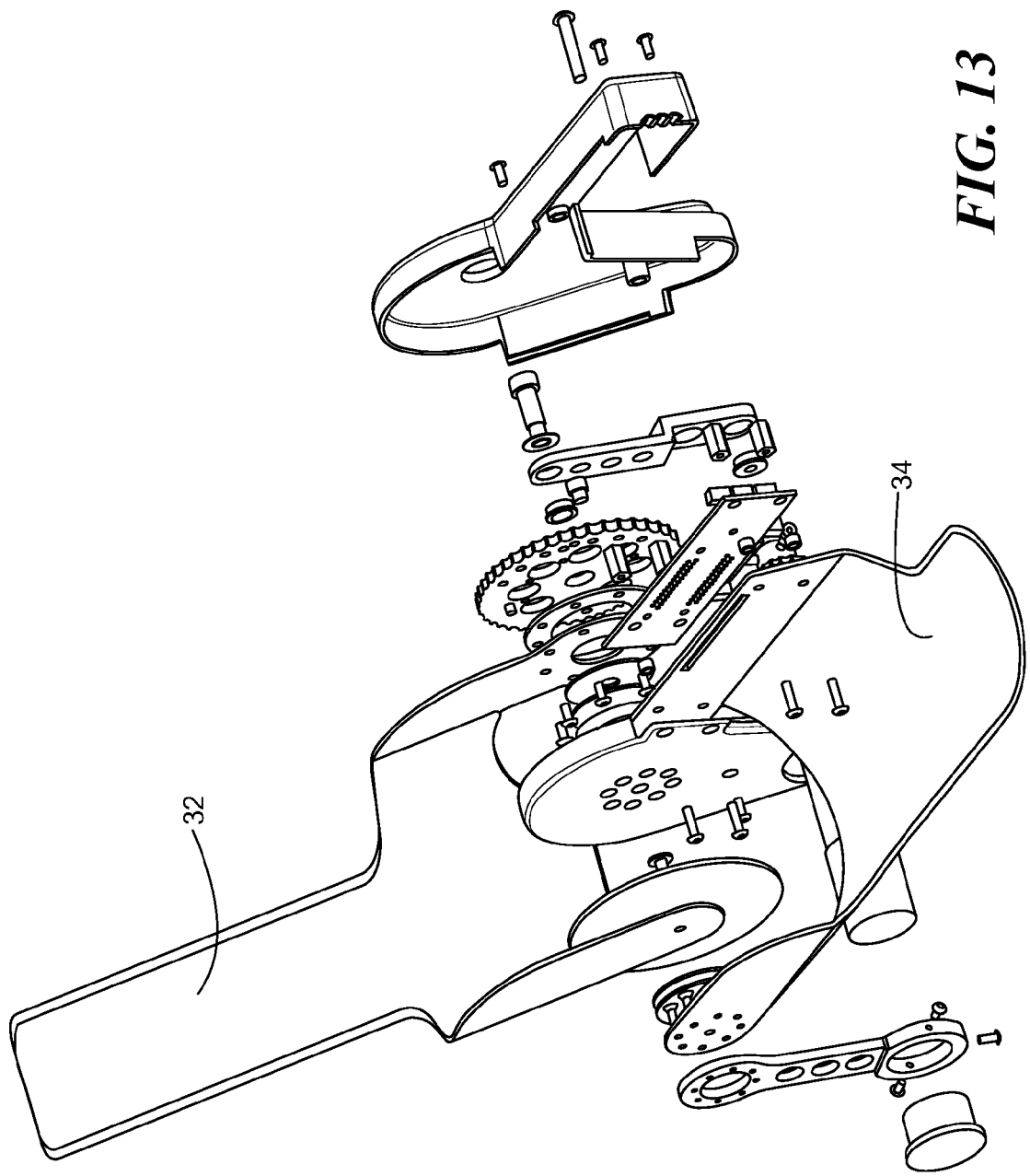
FIG. 13 shows an exploded view of the wearable component according to illustrative embodiments of the present invention.

As shown in FIG. 12, the brace 7 may move in a flexion direction and an extension direction, which define an inside region 65 and an outside region 66 of the brace 7, respectively. For example, when using an elbow brace, the motion of the brace that corresponds to the flexion direction is when the forearm approaches the upper arm (e.g., when the arm bends and the bicep muscle is contracting). Similarly, the motion of the brace that corresponds to the extension direction is when the forearm moves away from the upper arm (e.g., the arm straightens and the tricep muscle is contracting). Accordingly, the inside region 65 of the brace 7 includes the region where portions of the brace 7 are facing one another during flexion, and approach one another during flexion. Similarly, the outside region 66 of the brace 7 includes the region where portions of the brace 7 are facing one another during extension, and approach one another during extension. (or are moving away from one another during flexion).

Figure 16:
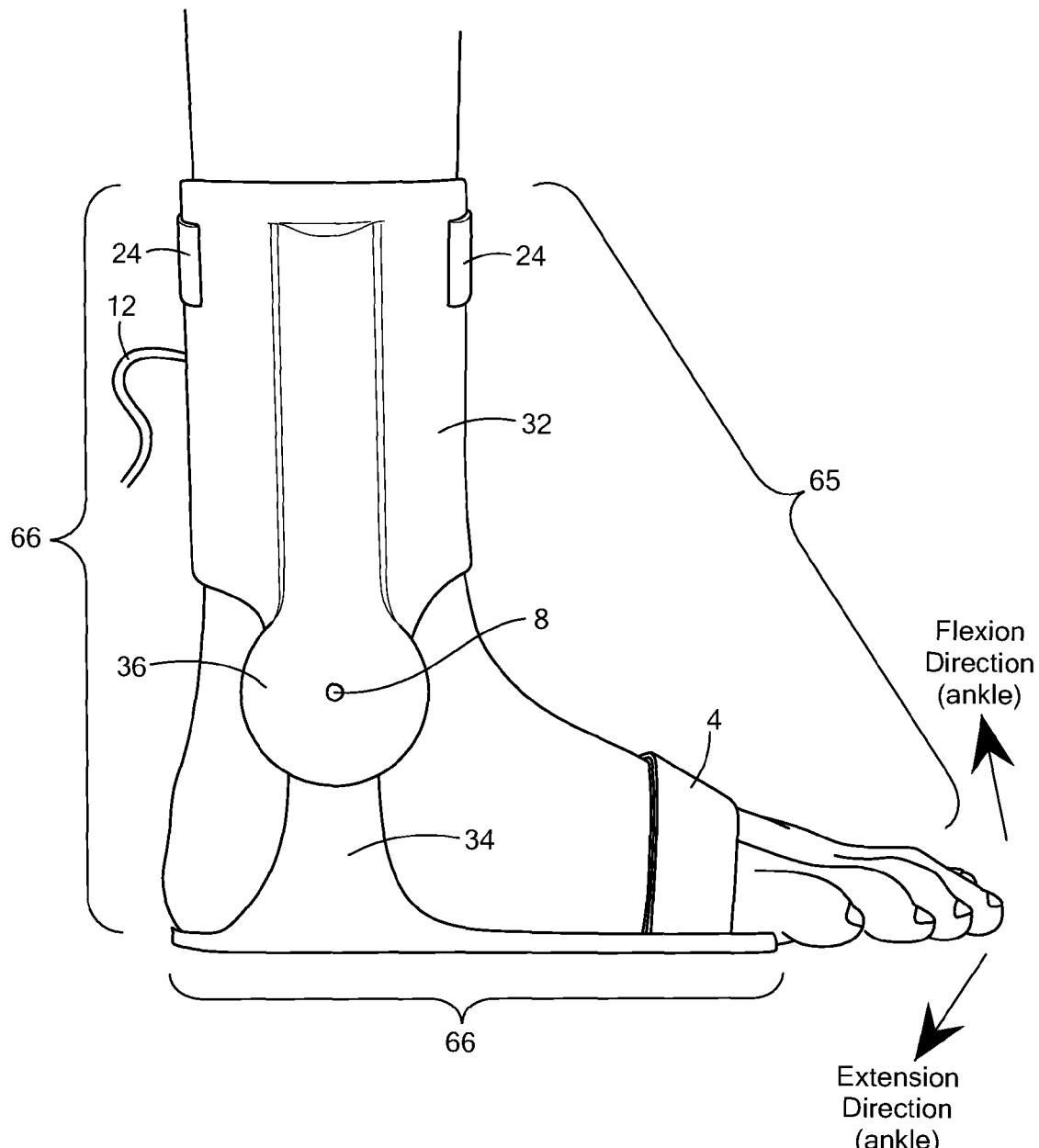
FIG. 16 shows a sketch of a wearable component around an ankle according to illustrative embodiments of the present invention.
Figure 17:
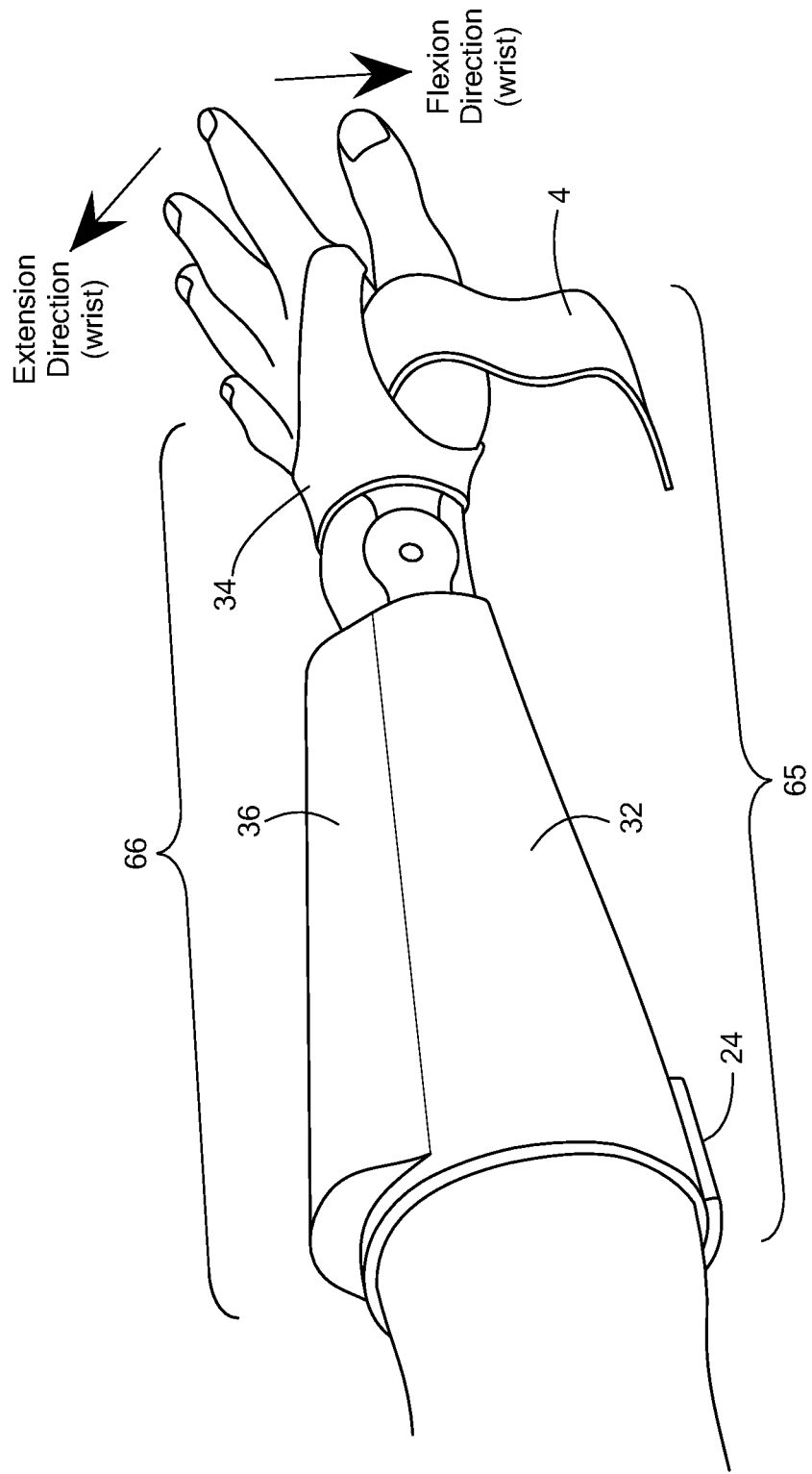
FIG. 17 shows a sketch of a wearable component around a wrist according to illustrative embodiments of the present invention.
Figure 18:
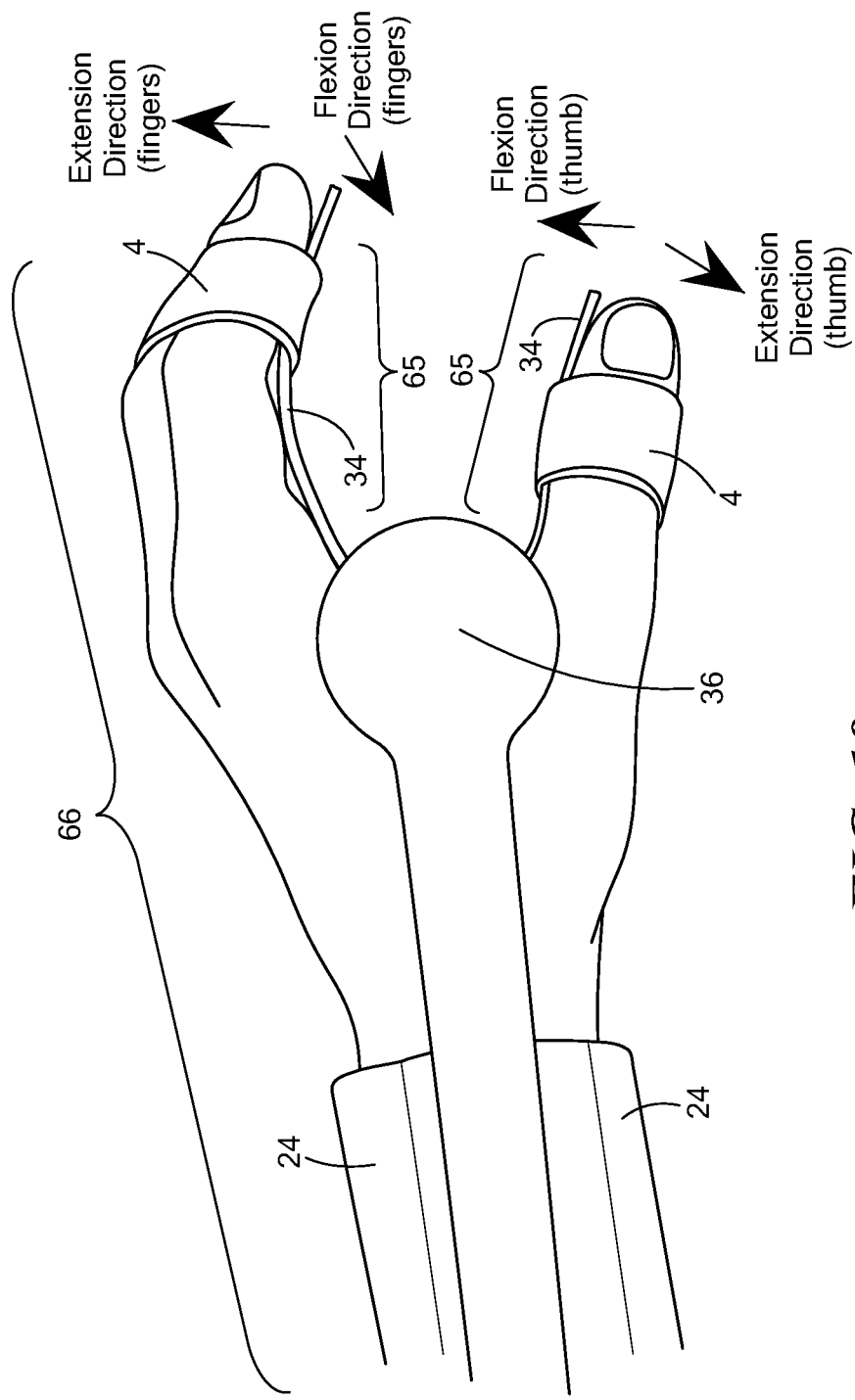
FIG. 18 shows a sketch of a wearable component around a hand according to illustrative embodiments of the present invention.

For example, in the case of the arm, the outside region 66 is the region proximate to the tricep, the olecranon (the point of the back of the elbow), and the underside of the forearm (with hand and arm in handshake position). In the case of the ankle (as shown in FIG. 16), the outside region 66 is the region proximate to the calf (back of the lower leg), the achilles tendon, the back of the heel, and the bottom of the foot. In the case of the wrist (as shown in FIG. 17), the outside region 66 is the region proximate to the top of the forearm (with arm held straight out in front, parallel to the floor, palm facing the floor), the back of the hand, and the back of the fingers. In the case of the hand (as shown in FIG. 18), the outside region 66 is the region proximate to the top of the forearm (with arm held straight out in front, parallel to the floor, palm facing the floor), the back of the hand, the back of the thumb, and the back of the fingers.

Similarly, the inside region for a knee brace (not shown) is the region proximate to the hamstrings, the back of the knee, and the calf (the back of the leg). The outside region for a knee brace is the region proximate to the quadriceps, the front of the knee (kneecap), and the front of the shin (the front of the leg). In this case, the motion of the brace that corresponds to the flexion direction is when the foot moves closer to the hamstrings (back of the leg) and the extension direction is when the foot moves away from the hamstrings (or the leg straightens).

Embodiments of the present invention may dispose the majority of the actuator assembly volume (e.g., the motor, gearhead, one sprocket and most of the chain) in the outside region 66 of the brace 7, although some portion of the actuator assembly volume (e.g., one sprocket) may be located coaxially with the brace 7.

There are numerous advantages to placing the majority of the volume and mass of the actuator assembly in the outside region 66 of the brace 7. Previously, this was difficult to achieve in wearable robotic devices since few actuation systems were designed that allow non-coaxial actuators, while remaining small and light enough for wearable applications. Embodiments of the present invention make this possible through novel geometries, high-strength materials, torque limiting characteristics, component configurations, attachment locations, in combination with a lightweight wearable system.

Figure 14:
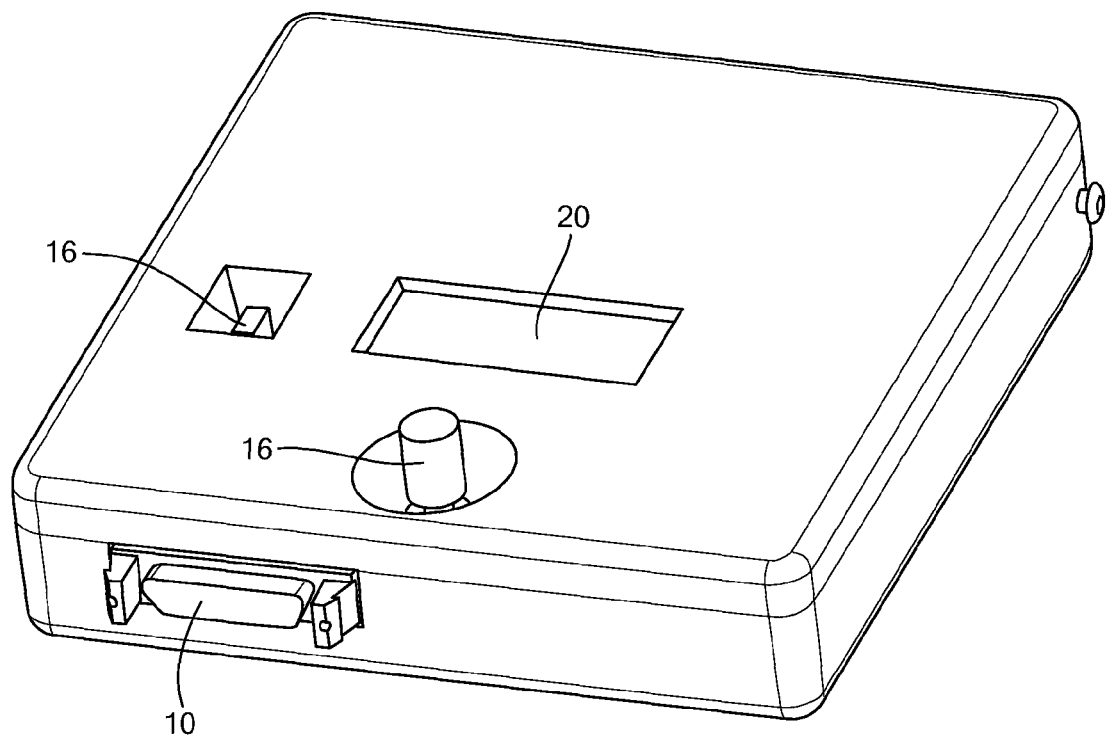
FIG. 14 shows a schematic view of a control system according to illustrative embodiments of the present invention.
Figure 15:
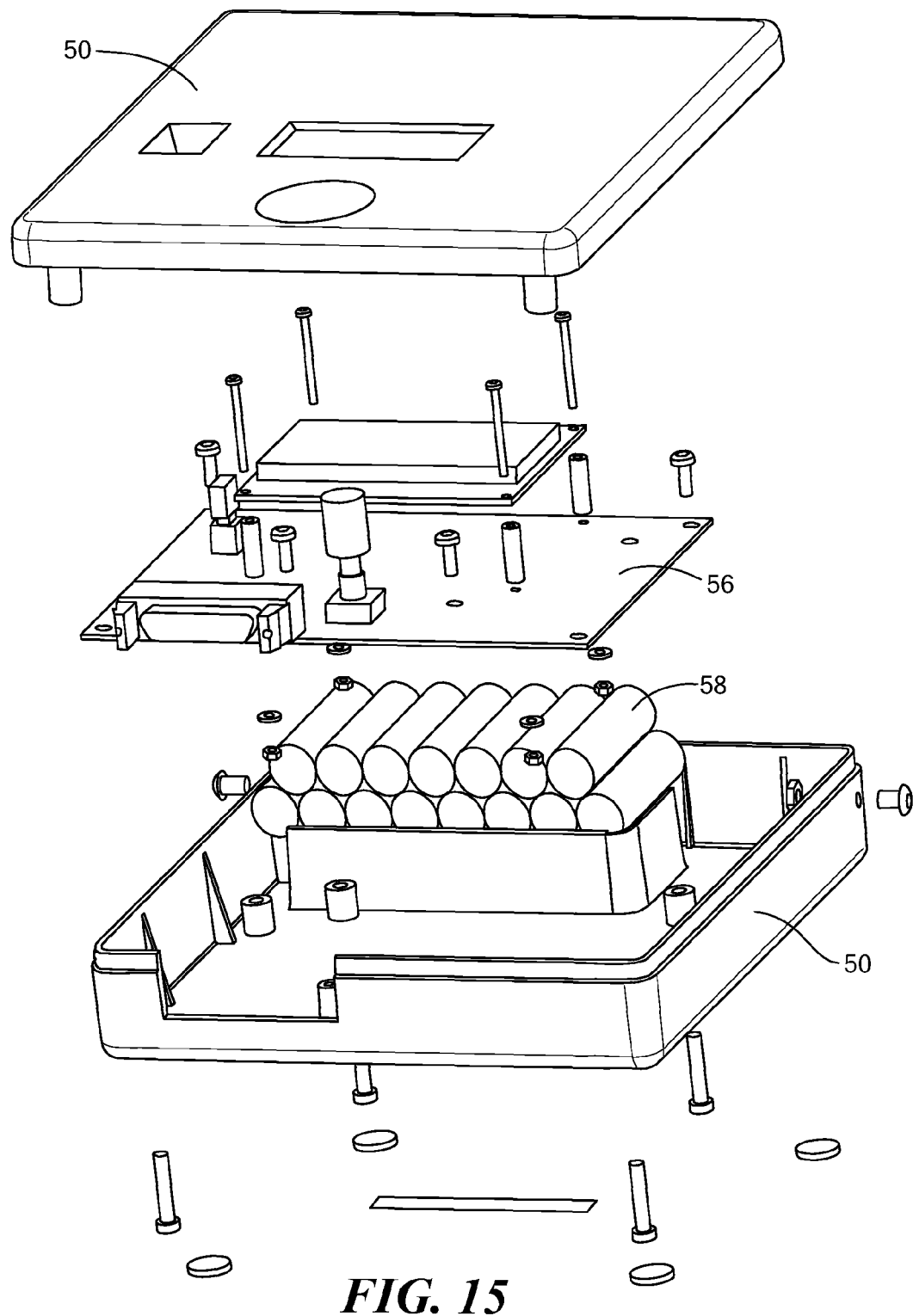
FIG. 15 shows an exploded view of the control system according to illustrative embodiments of the present invention.

As shown in FIGS. 14 and 15, the control system 18 includes a user interface through which a user interacts with the device. The user interface may include inputs 16, such as single or multiple knobs, buttons, switches, touch sensors, touch screens, or combinations thereof, for user input and feedback, and may include outputs 20, such as audio and/or visual devices, e.g., speakers, lights, LEDs, tactile sensors or transmitters, visual displays, such as LCD screens. The control system 18 may also include a processor 56 which processes the signals from the sensors 24, communicates with the user interface 16, 20, applies control algorithms and sends output commands to the actuator assembly 36. The control system 18 may also include a power source 58 and a data storage and management system (not shown) which may interact with the processor 56.

Although embodiments of the device are described and shown with various components in the control system 18, some components, such as the power supply 58, user interface, processor 56, may be located on the wearable component 2, on the control system 18, or both. As previously mentioned, electrical and mechanical cables 12 may connect the control system 18 to the wearable component. Mechanical cables may be part of the actuator assembly, e.g., pull-pull throttle cables. Electrical cables may carry sensor signals, motor power, ground, shielding, or sensor power. Various ports and/or connectors may be used on the control system 18 for connection and communication to external devices, additional wearable components or systems, charging systems, and/or additional sensors. Further, an additional control unit, containing a user interface and feedback mechanisms, may be connected to the main control system 18 using such connectors. The control system 18 may include an enclosure 50 to house the various electrical and mechanical components. The control system 18 may allow the user or trained person to change settings on the device, observe the device and/or user status, manage stored information, turn the device on or off, or make other technical or clinical changes. The control system 18 may also provide the user and/or caregiver with information regarding range of motion, safety concerns, number of repetitions, clinical updates, rehabilitation progress or other technical or diagnostic information.

The beneficial attributes of embodiments of this device configuration enable a practical implementation of the technology as a functional and rehabilitation aid. For example, placement of the motor 36 in a position near the axis of rotation 64 of the joint allows for a minimal drivetrain 42, 44 enabling a light weight, compact system. Placement of the motor 36 in a metallic tube housing 26, shields the motor 36 and the user as well as other sensitive electronic components from electromagnetic radiation, while providing protection for the system against impacts and foreign objects. The housing 26 also acts as a support structure for the brace 7, simplifying the process of donning and doffing of the wearable component 2. Further, the housing 26 acts as a handle, to facilitate clinician assistance, and to help in carrying the brace 7. The clinician assistance may include supporting or carrying some of the weight of the device when the subject is wearing the device, e.g., to relieve weight or stress from a subject's shoulder during the execution of physical tasks. In addition, the drivetrain components 42, 44 are placed on the outside of the limb, such as an arm, to minimize the risk of abrasion of components against the user's body. For example, the drive assembly 42, 44 may be located on one side of the device for a right arm version and on the other side of the device for a left arm version. Placing the actuator assembly in an area where collisions are highly unlikely between the actuator assembly and the limb segments potentially decreases the likelihood of injuries to the limb segments. For example, collisions may be more likely if parts of the actuator assembly were in the inside region of the brace or located within the flexion direction since limb segments often move through that region.

Embodiments of this configuration also provide a well balanced brace, which improves ergonomics. For example, the actuator assembly may be centered on the back of a limb or in the outer region, rather than coaxial with the limb where the assembly would stick out to the side. In addition, the configuration may be less likely to collide with other body parts during motion since a majority of the volume of the actuator assembly may be positioned in what we have termed the outside region of the brace rather than to the side of the joint. Collisions with other objects (e.g., door frames, arms of chairs, walls, vehicles, other people, etc.) may be less likely when a majority of the volume of the actuator assembly (including, for example, its motor) is in an outside region rather than in the coaxial configuration. Also, for certain joints, the configuration may be more aesthetically pleasing.

In order to achieve high torques, the drive assembly may include a planetary gear head directly coupled with the output of the motor 36, and the final stage of reduction in the drivetrain is achieved with a chain drive 42, 44, which has a higher torque capacity than the planetary gear head. For example, the actuator assembly may be comprised of an electric motor and the gear reduction that is coupled to apply torque about the joint via a shrouded geartrain may use a chain and sprockets.

The EMG sensors 24 may be located on the user's muscle, e.g., bicep or tricep, for use in flexion or extension modes. For example, the bicep configuration may be achieved by attaching (e.g., using hook and loop fasteners) the sensors 24 to the inside of the elastic strap 4 that couples the brace 7 to the bicep. Similarly, the tricep configuration may be achieved by attaching (e.g., using hook and loop fasteners) the sensors 24 to a hook-sensitive pad 22 (e.g., with compliant, compressive elastic material under it to ensure continuous pressure against the skin) inside the second section 34 of the brace 7, so that the sensors 24 are contacting the tricep.

The control algorithm used may apply a torque in a first direction that is proportional to a magnitude of the EMG signal, and may provide a constant force in a second direction. Some of the electronic hardware 38 (for example, EMG processing hardware) may be located on the wearable component 2 of the device, to avoid electromagnetic noise problems associated with sending signals over the long cable 12 between the control system 18 and the brace 7.

In addition, the larger, heavier components of the device may be located in the external control system 18, to minimize the size and weight of the wearable component 2. The control system 18 may be equipped with a shoulder strap 14 to improve portability of the device.

Although embodiments have been described and shown with regard to an arm and motion about the elbow, the device may be adapted for use with other body parts and joints. For example, FIG. 16 shows the wearable component around an ankle, FIG. 17 shows the wearable component around a wrist, and FIG. 18 shows the wearable component around a hand. For example, when the device is adapted for use about the ankle, the straps 4 provide coupling of the brace 7 to the leg and the foot, allowing the sensing system sensors 24 to obtain and measure signals from the user's muscles on the leg and/or the foot. The actuator assembly then applies a torque or force to the sections 32, 34 of the brace 7 about the ankle joint.

Similarly, when embodiments of the device are adapted for use about the wrist, the straps 4 provide coupling of the brace 7 to the forearm and the hand, allowing the sensing system sensors 24 to obtain and measure signals from the user's muscles on the forearm and/or the hand. The actuator assembly then applies a torque or force to the sections 32, 34 of the brace 7 about the wrist joint. When embodiments of the device are adapted for use on the hand, the straps 4 provide coupling to the fingers and the hand, allowing the sensing system sensors 24 to obtain and measure signals from the user's muscles on the hand and/or the fingers. The actuator assembly then applies a torque or force to the sections 32, 34 of the brace 7 about the finger joints. In other embodiments, the device may couple only to one side of a joint.

In one embodiment, torque is applied to induce motion about the joint via the motor 36 and the gearhead, and a chain and sprocket reduction 42, 44. Screw heads 40 may be used as the hard stops or limits, which collide with the structure of the brace 7 to limit its range of motion. The drivetrain and potentially dangerous moving parts are covered by the protective covers 28, which may be made of plastic shells.

There may be multiple modes of interfacing with various embodiments of the device. Parameters, such as control, brace strength, system gains and sensitivities, virtual spring parameters and strengths, EMG threshold values, maximum and minimum torques, operational range of motion, damping parameters, user feedback modes, data logging parameters, may be varied and adjusted by the user and/or a trained individual via the user interface 16, 20. Any of these parameters may be adjusted independently of one another or in conjunction with one another. For example, the user and/or trained individual may adjust the force parameters, such as the assistance level in the flexion direction and the extension direction, independently of one another. The user interface may be used to make adjustments to the aforementioned parameters, and to give feedback to the operator of the device. The parameters may be adjusted by the user and/or trained individual at any time, e.g., before, during (including while the brace is moving and/or stationary) and/or after the time the brace is in use.

During operation, there may be continued interaction between the user and the device in some embodiments of the present invention. For example, sensors detecting the range of motion of the joint may give the user feedback (audio, visual or both) regarding the range of motion of his or her exercises. Counters may keep track of the number of exercises completed and provide the user with that feedback (audio, visual or both). Timers may keep track of the elapsed time and provide the user with that feedback. The system may provide the user or caretaker with useful information that could be used to track progress, e.g., EMG amplitude or profile, velocity/torque/force/position information. Audio or visual cues may also be used to inform the user of the system status, e.g., battery charge level, errors, damage to the device or sensors, maintenance requirements.

Embodiments of the device may employ various control algorithms for controlling the force applied in one direction and the force applied in the other direction. The control algorithms may provide an asymmetric control of the device. For example, the output (command to actuator system) may be a function of the EMG signal measured (e.g., flexor or extensor muscle) and may also include parameters related to time, position, velocity, acceleration, forces measured, torques measured, temperature, user inputs (e.g., push buttons), signals from other medical or electronic devices (e.g., other orthotic devices, pacemakers, palm pilots, computer system, etc). The force in one direction may be based on the EMG signals from a first muscle, and the force in the second direction may be based on the EMG signals from the first muscle, may be related to the EMG signals from a second muscle, and/or may be based on an absence of any sensed EMG signals. The force in the second direction, however, does not use the same relationship as the first direction, thus the two forces are asymmetrical. In addition to the EMG signal relationship, the forces in either or both directions may additionally be based on other inputs.

For example, embodiments of the device may have a mode of operation in which the device passively moves the limb through a range of motion at a predetermined speed or through a pre-determined trajectory, until the EMG sensors detect user activity or user-generated signals. Upon detection of such activity or signals, the device may change its mode of operation so as to behave in a more responsive manner to the user's activity or signals, (e.g., as discussed above where the force in one direction may be based on the EMG signals from a first muscle, and the force in the second direction may be based on the EMG signals from the first muscle, may be related to the EMG signals from a second muscle, and/or may be based on an absence of any sensed EMG signals).

The user interface 16, 20 may be used in any number of ways. For example, in operation, a clinician or user may select any number of modes for operation of the device, such as a bicep mode or tricep mode, from the user interface. In a bicep mode, the device may provide EMG-proportional assistance in the bicep direction and a return force in the extension direction. In tricep mode, the device provides EMG-proportional assistance in the tricep direction and a return force in the flexion direction. The device may also have a bicep and tricep mode allowing for multiple inputs. The return force may be a constant force, a spring, a nonlinear force, etc. Various control algorithms are discussed in more detail below.

Embodiments of the device may also have a facilitation mode. Stroke patients often have difficulty extending their limbs, due to a lack of ability to flex their tricep muscles. Often if the patient has something to push against, e.g., a therapist's hand, the patient can activate the appropriate muscles to extend the limb. This process is called facilitation, and is often accompanied with verbal encouragement, and/or tapping/pushing/shaking of the appropriate limb segment or muscle group.

Embodiments of the present invention may apply torque against the user's limb (with or without feedback) as a means of providing the user with a force to push against or resist. This application of force or torque may be accompanied by other feedback means (for example a light which changes color indicating it's time to start pushing, or a voice from a speaker saying "Now don't let me move your arm," as the brace begins to push the user's arm in a particular direction). To further accompany the brace motion and to further encourage motion of the user's limb, the device may stimulate the user by having actuators which tap, squeeze, vibrate or apply pressure to various parts on the limb in conjunction with, or in lieu of, the application of torque. For example, the device may stimulate nerves associated with the stretch reflex in the appropriate (e.g., impaired) muscle to assist in providing motion. The device may assist the user in drawing attention to or focusing on the muscle group that should be used. Other stimuli (e.g., actuators, estim, vibro-tactile actuators, sounds, sights, etc.) may be used during facilitation or during general use of the device. For example, a vibrator on the tricep muscle may vibrate when the user is asked to extend the arm—to remind the user that this is the muscle to activate.

In use, embodiments of the device should be calibrated for each session, to compensate for the user's natural electrical offsets (in order to distinguish rest conditions from EMG muscle activity). The device may calibrate automatically by holding the user's arm, or having the user hold his or her arm, at a neutral position (e.g., approx. 90 degrees) with the brace in its calibration mode. For example, the device may calibrate in a designated time with the limb held at a predetermined position, such as in about 10 seconds with an arm held at 90 degrees. This calibration step (e.g., maintaining proper angular orientation of the arm during calibration) provides the proper device operation because there is a muscle-length dependent electrical output offset (EMG)—so a mid-range calibration offset is desired to attain consistent operation through the muscle's full range of motion. The method of calibrating the device by having the user hold the limb in a mid-range of motion relaxed pose allows a DC offset to be subtracted that corresponds to a mid-range electrical offset.

Embodiments of the system may also dynamically adjust the calibration values during operation, if changes in the user's electrical offsets are detected. For example, the calibration may be dynamically adjusted if the device detects changes in tone, sweating, temperature, stress, fatigue, excessive sensor movement (or frequent disconnect), pulse rate, blood oxygen levels, excessively high or low gain settings by the user, etc. If the system automatically detects user muscle fatigue and changes the calibration values, the system parameters may be changed to reflect that. In addition, the system may dynamically adjust certain system parameters such as signal filtering parameters. If the system detects changes in the signal characteristics, or in environmental or user characteristics, it may dynamically adjust filtering parameters (filter bandwidths, for example).

After calibration of the device, the operation screen may appear on the display 20, in which the user may set the values of one or more parameters, e.g., "gain" and "return." The "gain" sets the level of assistance in the first direction of motion (the scaling factor which scales the EMG reading) to give a proportional output command to the actuator assembly 36, 42, 44. "Return" sets the magnitude of the force in the second direction of motion, which may not be proportional to the EMG signal, e.g., a constant force or another control algorithm. The device may also be capable of further signal processing, such as low-pass filtering or smoothing of EMG signals, as is well known to those skilled in the art, to enable the device to provide a consistent or smooth force to the brace 7.

Embodiments of the present invention may also be combined with other therapeutic, supportive or functional devices which cause motion or stimulation by other means, or provide support to one or more body parts of the user. For example, the device having an elbow brace (as disclosed above) may be used in conjunction with a balanced forearm orthosis, or other body weight support system, to assist with moving the body part by reducing or eliminating the force of gravity on the body part. Alternatively, or in addition to, the device (e.g., having an elbow brace) may be combined with a functional electrical stimulation (FES) device, such as a hand grasp. The two devices may work together to encourage and stimulate natural movement patterns. For example, the devices may interact in a way that causes the hand to close (via electrical stimulation) only when the elbow reaches a preset angle, or only when bicep activity reaches a certain level, or only when the tricep is relaxed to below a certain threshold value. Alternatively, the hand closing may be user-activated (using FES) by a push-button switch, and may be opened (using FES) only when the elbow device measured the bicep relaxation to be below a threshold value. In other embodiments, the device may have programmed trajectories, such as a "reach and grasp" trajectory. In this case, the user initiates a reach, which is recognized as such by the elbow device, and this in turn causes hand FES device to close when the elbow nears full extension. The hand may then release its grasp when the bicep and/or triceps are relaxed to below a threshold value.

Embodiments of the present invention may also be used for assistance with recreational movement patterns, e.g., dance, sports, video games, musical performance, art creation activities, etc.

Electrical stimulation and orthotic power assist may also be used in conjunction with the device on the same muscle group or groups. For example, FES electrodes may be placed on the triceps, and a powered orthotic device may be worn on the arm. Electrical stimulation may be used as a means to initiate motion, or to promote user awareness, or to "wake up" the muscle. Once the muscle is slightly active and under the user's control, the amount of FES could be decreased and replaced by less painful assistive torques applied by the orthotic device.

Embodiments of the present invention may also combine EMG sensing (lower level sensing at muscle level) with neural stimulators (higher level sensing at the brain level). For example, the neural stimulators may include cortical stimulation or peripheral stimulation. The stimulators may be mechanical, electrical, chemical, acoustic, electromagnetic, and/or magnetic in nature. Similarly, embodiments may include the combination of mechanical actuation, such as application of torques/forces to the limb itself by the device with neurological stimulation, such as higher level electrical, chemical or mechanical stimulation at the brain level. For example, the device may be used in conjunction with deep brain stimulation, cortical stimulation, or peripheral stimulation, and the EMG sensing may be used in a closed loop control system to control, or be controlled by, the parameters used (e.g., frequency, duration, magnitude) in the brain stimulation or peripheral stimulation.

Embodiments of the device may also share user interface(s) with other devices, e.g., the other device(s) may use the user interface 16, 20 and/or the device uses the other devices' interface. Multiple devices, e.g., some may be powered orthotic devices and some not, may share a common user interface. This shared user interface may be wearable, may be wired or wireless, may be a personal computer, handheld computer, cell phone, etc. For example, systems that may share the user interface with the powered orthotic device may include pace makers, glucose monitors, electrical stimulation devices, heart rate monitors. Also, the user interface may serve as an input and output device, both accepting commands from the user (e.g., changing system setting, etc.) and providing information to the user (e.g., displaying information on a screen).

Embodiments of the present invention, may have all EMG processing, motor control, user interface, actuators and electronic hardware located in a control system 18 that is separate from the device. Preferably, the weight and size of the wearable component 2 is minimized. The control system 18 may be worn over the shoulder, or may be stationary with respect to the user. Mechanical torques and forces may be transmitted to the brace 7 via flexible drivetrains. In other embodiments, all processing, motor control, actuators, sensors and power sources may be located on or in the wearable component 2 to provide a fully portable system that involves no peripherals.

A battery pack may be connected to the wearable component and/or may be connected via a cable to the control system 18. For example, there could be a small battery pack with limited capacity that could be worn on the wearable component 2 (or is internal to the component 2), maximizing portability and completely eliminating the need for wires. There could be a higher capacity battery available that would allow longer run time, but may be too heavy or large to be worn on the wearable component 2. This battery pack may plug in and be worn on a belt, in a back pack, in a pocket, or elsewhere on the user's body. A larger battery pack may also be stationary with respect to the user, e.g., on a table top.

Embodiments of the device may have a mechanical structure such that the supporting joint about which the device rotates is the user's joint. In other words, the device may couple to the user's body above and below a joint, and may apply force or torque at those points, so as to cause motion about that joint. The device may not have hinges or pivot joints of its own.

Embodiments of the device may be integrated into articles of clothing, such that the donning of a particular piece of clothing (long-sleeved shirt, for example) would constitute donning the device, and the sensors and actuators would be held in place by the clothing itself. In this case, the power source (e.g., batteries) may be integral to the clothing or be removably attachable to the clothing.

Embodiments of the device may also have a system and/or protocol for ensuring proper alignment of the device with the appropriate joint. For example, the protocol may consist of visual markings on the device for alignment with key anatomical features, fixed angles for automatic brace alignment when the limb is pressed firmly in the brace, support structures for holding the device in place while the user pushes the limb into place.

Figure 19:
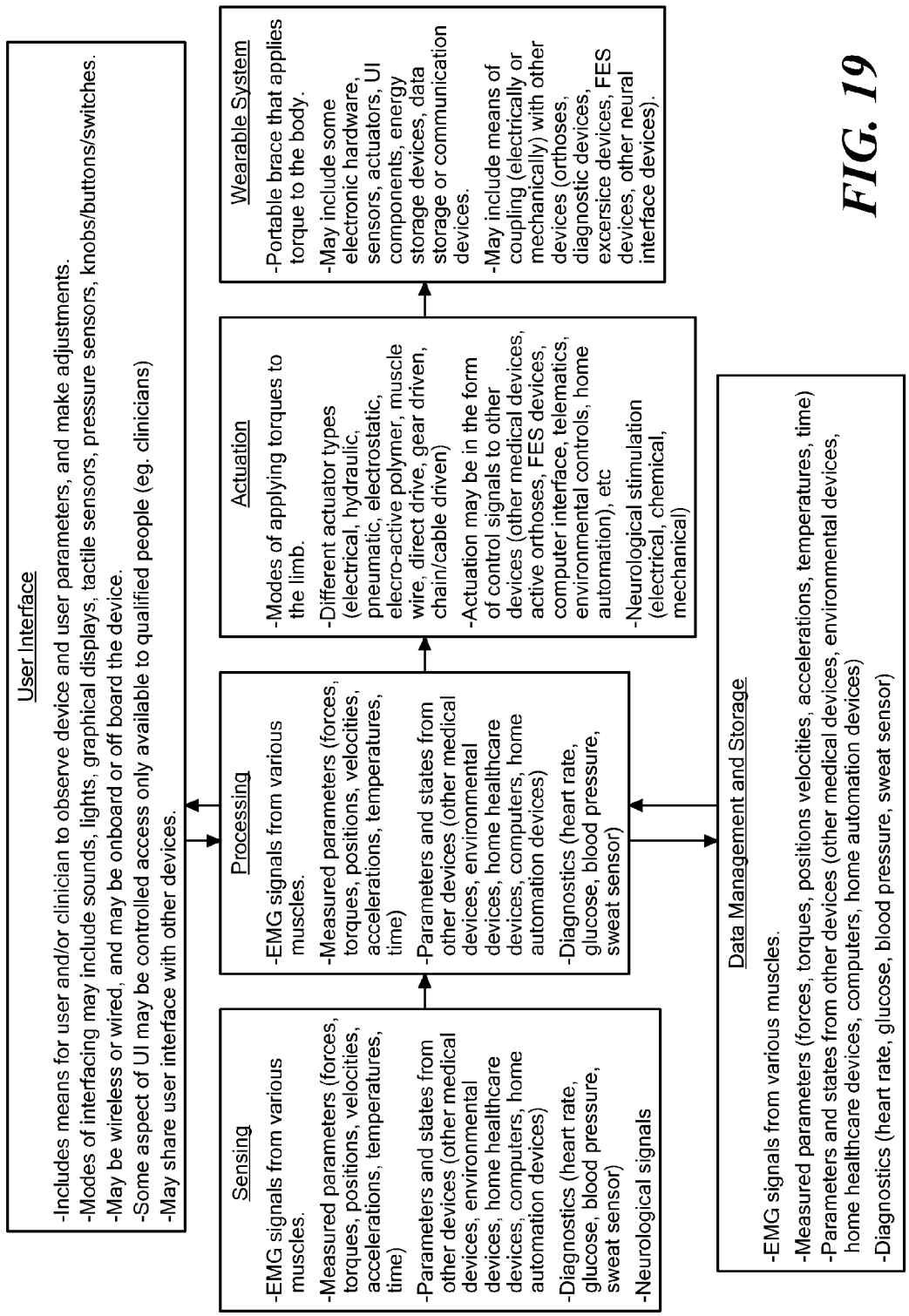
FIG. 19 shows a block diagram of the powered orthotic device system components according to illustrative embodiments of the present invention.

FIG. 19 shows the basic components of the device according to an embodiment of the present invention. In general, the sensing system collects information from a plurality of sensors 24 and sends those signals to a processing system. The information the sensors 24 collects may be from the user, the brace, the actuator assembly, the processing system and/or the environment. The processing system, in turn, processes those signals and generates an output signal to the actuator assembly. The actuator assembly applies torques and forces to the brace 7. Additionally, the user interface may include input and output devices which allow the user to provide input to the processing system and which allow the processing system to present information to the user. The data storage and management system may record and store data received from the device and/or the user.

The user interface may allow multiple levels of access control to the device parameters or usage/user data stored in the device. For example, the user may be allowed to control certain parameters (e.g., assistance levels, spring strengths, operational modes, volume, feedback mode, etc.) that may be adjustable via a compact user interface on the device or its peripherals (control system 18), while other parameters may have a controlled access and may only be adjustable by qualified individuals who either have a key or code, which may be a contact device (e.g., key or fingerprint reader) or non-contact device (e.g., using a barcode or radio frequency identification (RFID) reader) to make those changes, or who have a handheld or desktop device (e.g., computer) which interfaces with the device via a wired or wireless connection. The user interface may permit the changing of system parameters, downloading of usage and user data and diagnostics, uploading of user profiles and use protocols, erasing of system memory, calibrating of the device, or running of user training sessions. For example, the user may be first outfitted with the device at the clinician's facility, wherein the clinician puts the device on the user and connects to a computer. This initial session may involve a device calibration and tuning of parameters, followed by a training session wherein the user uses the device, e.g., plays a game moving cursors and hitting targets on the computer screen to become familiar with the motion of the device. A rehabilitation protocol may be uploaded to the device via the clinician's computer connection as well. The patient may then operate the device for subsequent sessions without the computer connection, performing functional tasks and rehabilitation exercises. Similarly, the user interface may have a secured access level that only qualified individuals or agencies may access in order to protect sensitive data related to the user.

Embodiments of the device may also interact with and connect to a computer or other remote user feedback system during operation. This may involve displaying progress information to the user or clinician during use, or may be used to facilitate or encourage motion of the limb, or to make therapy sessions more intuitive, functional, interesting, or entertaining, e.g., by playing a game. This may also permit a clinician to remotely control or monitor use of the device by the user. For example, the user may connect the control system to the Internet, either through a cable or wirelessly, so that the device may communicate with a clinician or other person remotely located. The clinician may then adjust settings, monitor a session, monitor system values/parameters, or control and drive the device. The clinician may also have a corresponding robotic or haptic device that allows the clinician to feel or visualize the motion/strength/speed/quality of motion, etc. of the user wearing the brace. This enables therapy sessions to take place even when the therapist and patient are remotely located.

Embodiments of the device may have a peripheral control unit (such as the control system 18) that may be used to interface with, provide power to, record data from, update parameters of, or provide actuation to multiple devices. For example, one control unit may communicate and interact with multiple powered orthotic devices, other medical devices, home automation devices, diagnostic and monitoring systems, environmental controls and sensors. Similarly, multiple control systems using hardware and/or software may interface with one or more devices. One power supply may also provide power to the device or multiple devices and multiple power supplies may provide power to the device or multiple devices.

Embodiments of the device may also have a data storage and management system which may record and store data from the device. The data storage system may integrate with other standard of care data formats and provide tracking, data-logging and/or synchronizing with other applications and devices e.g., in home automation. In use, the device may measure and store user data during operation. Data may include progress metrics (e.g., range of motion, speed of motion), medical diagnostics (e.g., vital signs, blood pressure, body temperature, sweating, pulse), general data logging (e.g., hours of use) and usage patterns (e.g., when and for how long, device settings). This information may then be presented to the user and/or clinician to help shape the therapy protocols, dosage, assistance levels, device parameters, sizing, etc. For example, the information may be used to calculate a ratio between the quantitative measurement of device assistance (e.g., measured by the EMG levels going in, Gain, spring, etc.), and a quantitative measurement of patient performance (e.g., elbow range of motion, amount of use of arm based on accelerometer data, average speed of motion, frequency of motion, smoothness of motion, etc.). The information may include a qualitative measurement, e.g., user indicates amount of assistance they are contributing to moving the device. The information may include a combinations of items, such as the amount of external help (e.g., other person assisting), the amount of device help (e.g., gain level of the device, measure torque, or force of the device, etc), and/or the measure of success (e.g., amount of use, range of motion, acceleration, speed, frequency, smoothness, etc.). The system may have the capacity to store (via permanent or temporary memory) many pieces of information (including all those mentioned above) pertaining to the user's progress, frequency and duration of use, parameters of use (e.g., range of motion, velocity/force/torque profiles, selected gains, damping coefficients and system settings), and EMG signal history. This information may be accessed later by the user, caretaker, therapist, physician or other individual who may use the information to track the user's progress, or to adjust system parameters accordingly. Multidimensional measurements may be measured and/or stored, with one or more of the dimensions measured by the device. The information may be recorded manually, or by other means (other devices, add-on components, etc). The information may be used to automatically modify treatment with the device, e.g., based on the multidimensional measurements, combinations thereof, and/or relationships therebetween.

Embodiments of the device may also include a number of safety mechanisms. The device may be equipped with sensor disconnect sensing. For example, the device may detect when a sensor 24 has lost contact with the skin, based on characteristics of the sensor signal. This algorithm may cause automatic cessation of torque generation if EMG sensor disconnect (decoupling from skin) is detected. The system may then respond in a safe manner, (e.g., by turning off power to the actuator assembly) until sensor contact has been restored. If reconnection is detected, then the cessation is itself discontinued, and the device returns to normal operation, after a time delay.

Figure 8:
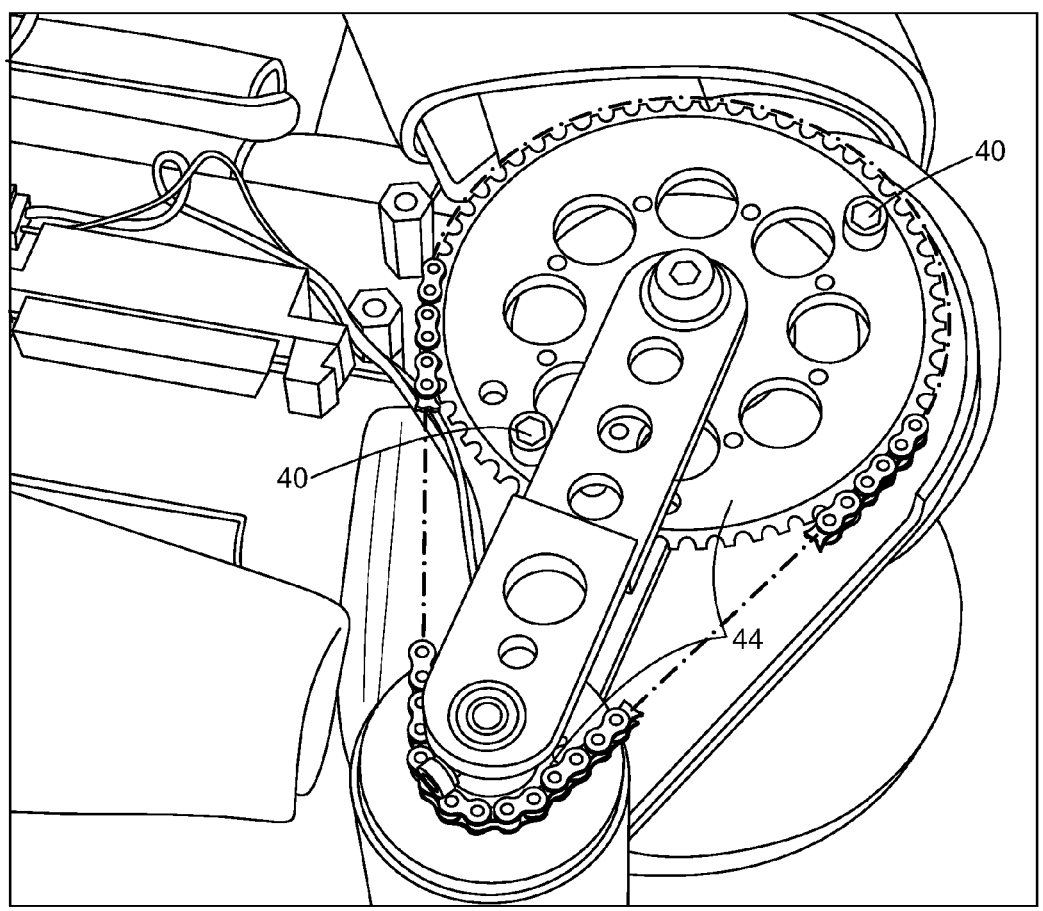
FIG. 8 shows the wearable component with drive train exposed according to illustrative embodiments of the present invention.
Figure 9:
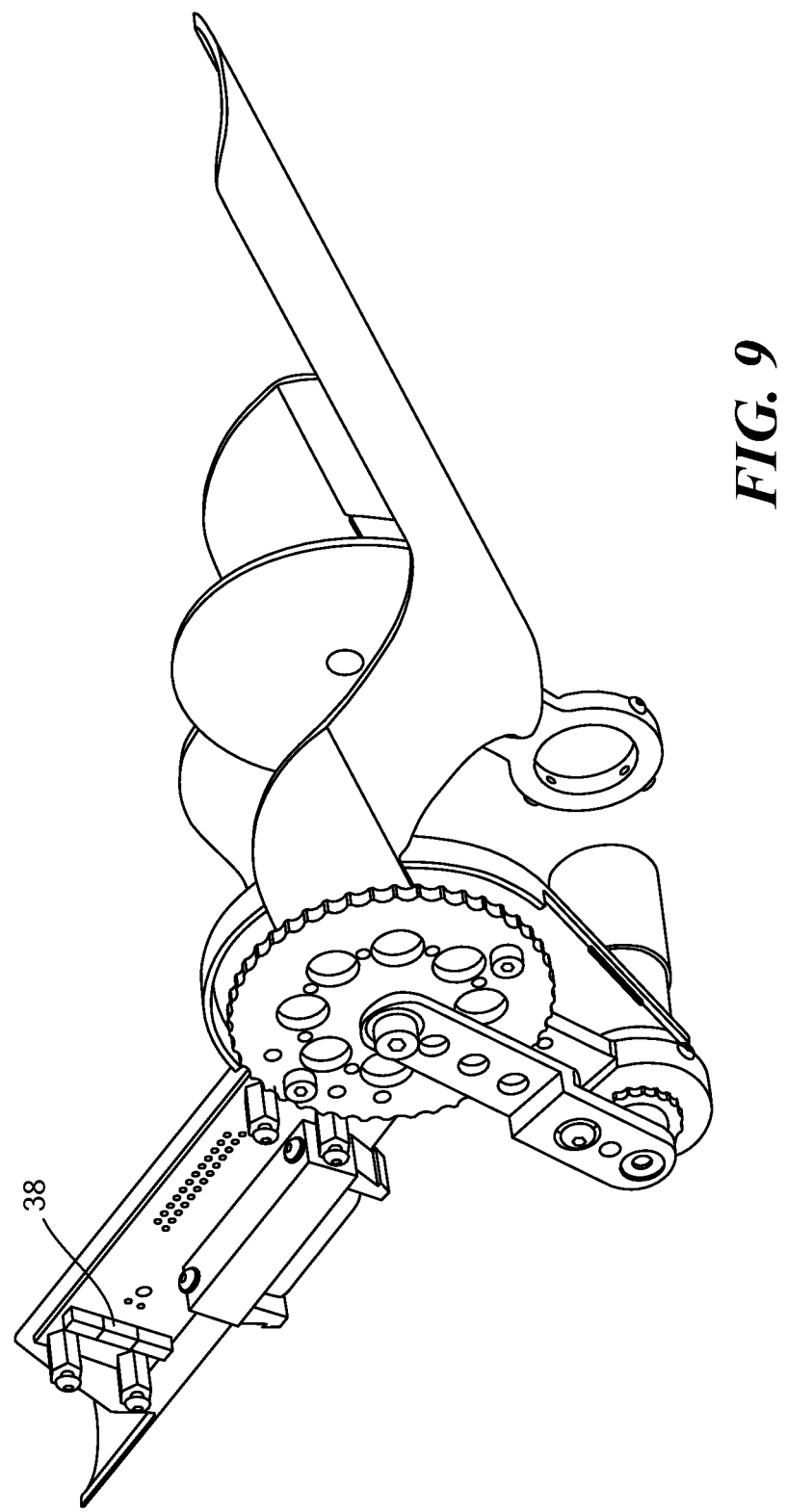
FIG. 9 shows a schematic view of the wearable component with the motor housing and the plastic cover removed according to illustrative embodiments of the present invention.
Figure 10:
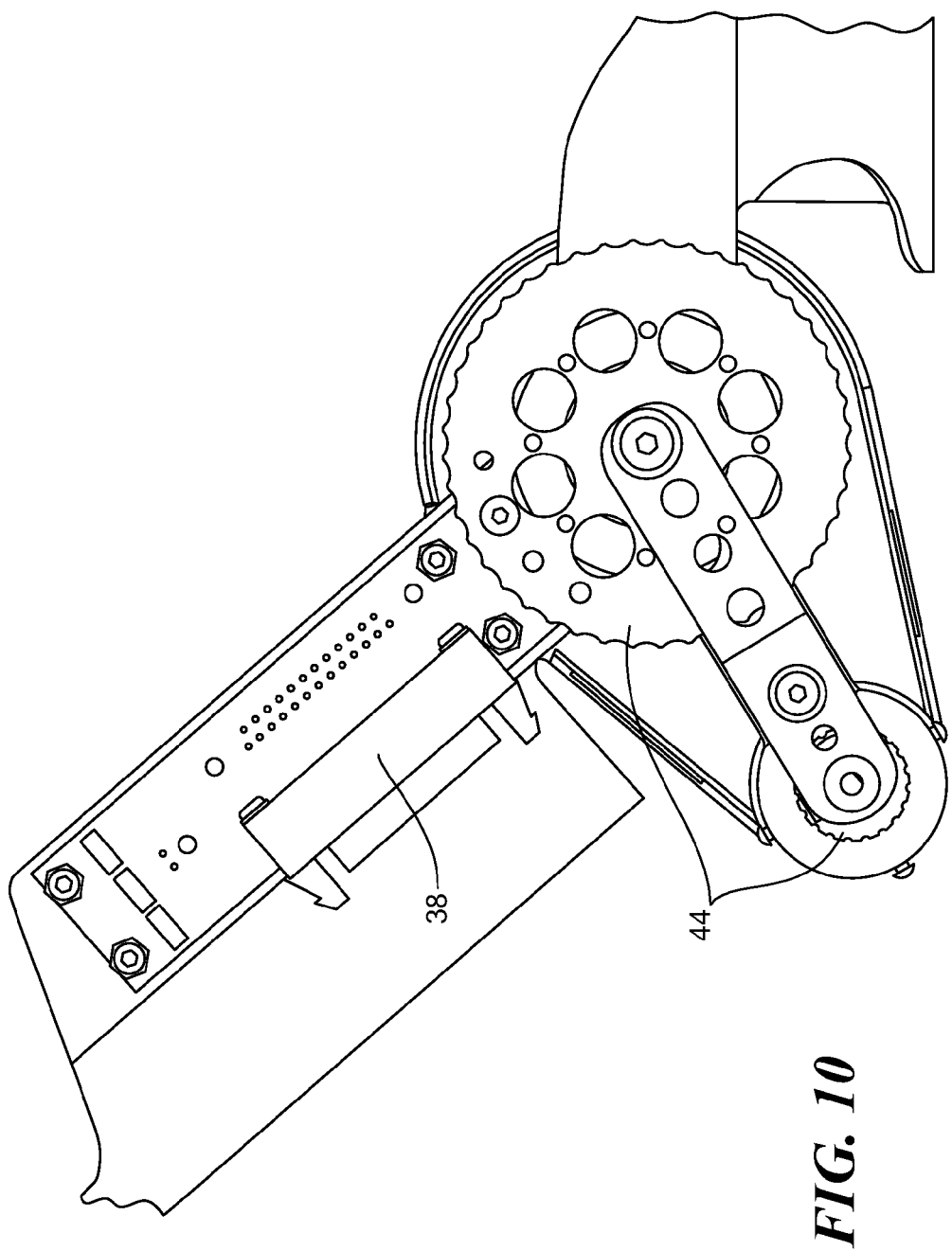
FIG. 10 shows a schematic view of the wearable component with the plastic cover removed according to illustrative embodiments of the present invention.
Figure 11:
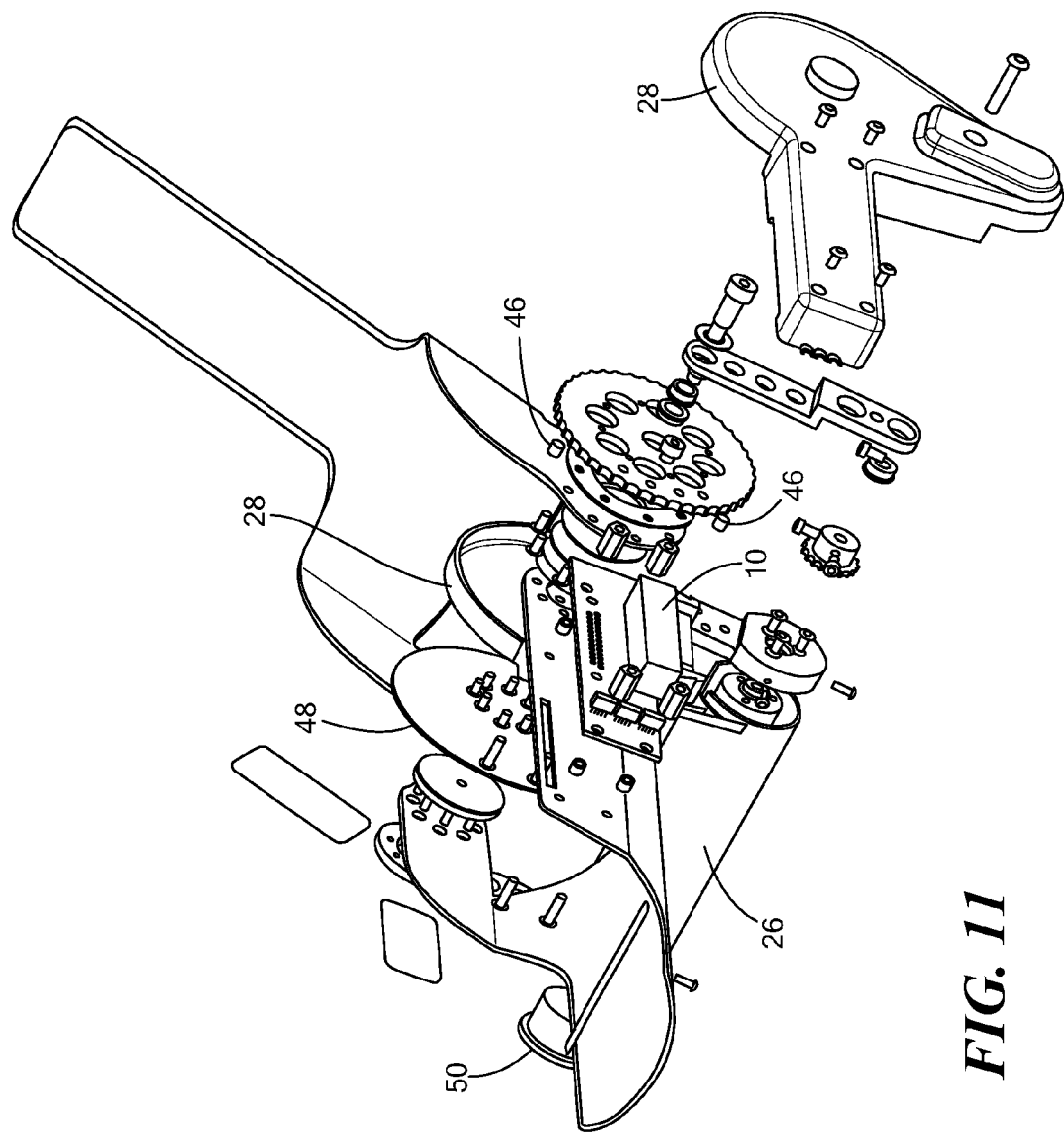
FIG. 11 shows an exploded view of the wearable component according to illustrative embodiments of the present invention.

Embodiments of the device may also be equipped with safe range of motion limits to prevent the possibility of injury by pushing a limb past the body's natural limits. For example, the device may have mechanical limits on the range of motion that may be adjustable by removing and re-inserting a physical stop, such as a screw 40, as shown in FIG. 8. Further, electromechanical or opto-electrical sensors (e.g., Hall sensor, optical sensor, potentiometer, laser range finder, switch, button) may be employed to provide feedback to the device regarding the position of the brace in its range of motion. This may enable the device to provide feedback to the user regarding his/her proximity to the end of the range of motion, and may also limit the output signal to the actuator assembly to prevent collisions with the mechanical limits. Certain sensors may provide some gradation of accuracy regarding proximity to the end of the range of motion (e.g., Hall effect sensor), while others may be simply on or off (e.g., switch). The device may also have range of motion limits that are supplied via software. Any combination of these physical or software motion limits may be employed.

Embodiments of the device may also limit the torque provided by the actuator assembly (e.g., for reasons of safety, protecting the user, as a means of protecting the system components from overloading due to excessive torque), by providing a control system that limits the current provided to the actuator assembly (e.g., consequently limiting the torque applied by the actuator assembly). There may be a "soft" limit that does not allow sustained high currents, although it may allow brief high-current spikes. There may also be an accompanying "hard" limit that provides an absolute current limit, which may be a current value above which the actuator assembly will not receive a current input. This allows the system to handle brief periods of high torque, but limits the maximum permissible torque at all times, as well as decreasing the allowable torque at any given time based on a recent history of applied torque.

Embodiments of the device may also protect against having the motor push continually against the limits of the device or the user's physical range of motion limits by providing a system that has sensors near the ends of the physical range of motion which command the control system to stop sending current to the motor (e.g., consequently stopping the motor from applying torque) when the brace is near the ends of its physical range of motion.

The processing system applies various control algorithms to the actuator assembly, and is responsible for the appropriate application, timing, and combination of the different control algorithms. Some of these control algorithms are described in more detail below. The actuator assembly receives its commands from the processing system, and applies torques, forces, velocities, and/or positions to the sections 32, 34 of the brace 7.

FIG. 20 shows an illustrative control algorithm and the variables upon which the algorithm is based that may be used in an asymmetric EMG-controlled device in accordance with embodiments of the present invention. The control output signal is the command that is sent to the actuator assembly. FIG. 20 depicts ways in which the various control output signal relationships may be combined to provide one command signal which commands the actuator assembly. As shown, a simple arithmetic combination may be used (1'), in which the output signals from the various relationships (some of which are shown in FIGS. 21-27 below) are added, subtracted, multiplied, divided, or any combination (linear or non-linear (2')) thereof, to generate the command signal to the actuator assembly. A conditional relationship may be used (3', 4'), in which the algorithm for combining the various output signals is dependent on certain conditions being met. Boolean combinations of such conditional relationships (4') may also be used. Also, any combination of the above mentioned techniques may also be used to combine the various output signals to generate one command signal.

Figure 21:
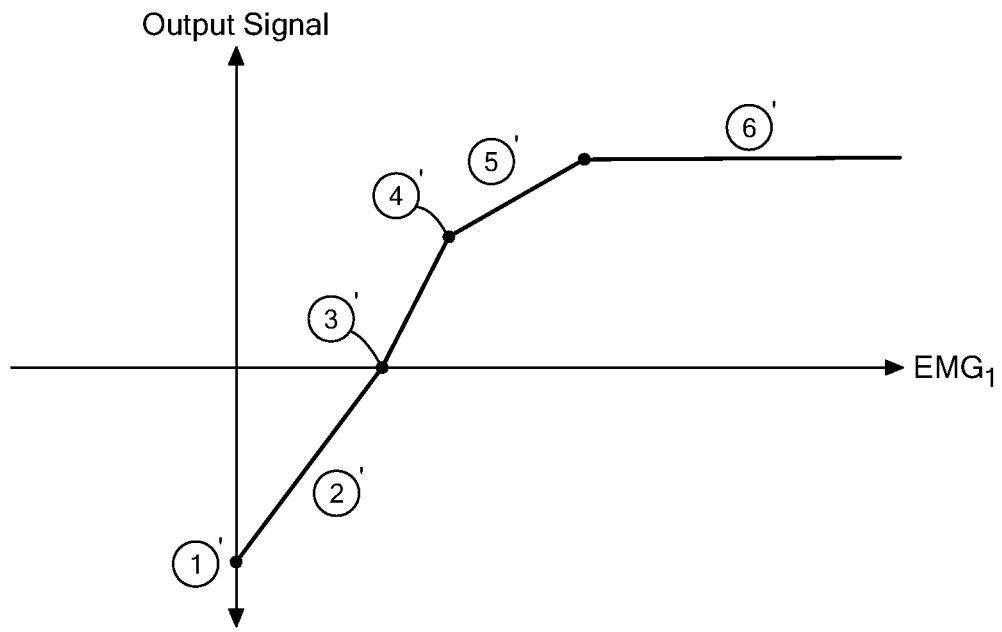
FIG. 21 shows a graph of EMG signal vs. output signal according to illustrative embodiments of the present invention.

FIG. 21 shows a graph depicting features of a control algorithm, namely the relationship between the control output signal and the measured EMG signal from a user's muscle (EMG1). In FIGS. 21-25, the axes have the following meaning: positive output signal correlates to actuator torque, velocity or motion in a first direction about the joint; negative output signal correlates to actuator torque, velocity or motion in a second direction about the joint; and EMG1 is the filtered absolute value of the EMG signal in the first direction. In FIG. 21, the y-intercept (1') is the maximum output signal in the second direction. This is the output signal that the system will give when the value of EMG1 is zero. The correlation between the output signal and EMG1 may be linear or non-linear, and may be considered in two separate regions: the first direction (4', 5', 6'), and the second direction (2'). The zero-crossing point (3') is the value of EMG1 at which the output signal changes direction. There may be break points (4') in any region, at which the slope of the relationship changes, or at which the relationship may change from linear to non-linear. There may be saturation limits (6') where the slope of the relationship goes to zero, meaning the output signal reaches a minimum or maximum "floor" or "ceiling" which it will not surpass, regardless of the value of EMG1. This may serve as a safety mechanism to prevent excessive torques in the case of abnormally high spikes in muscle activity.

Figure 22:
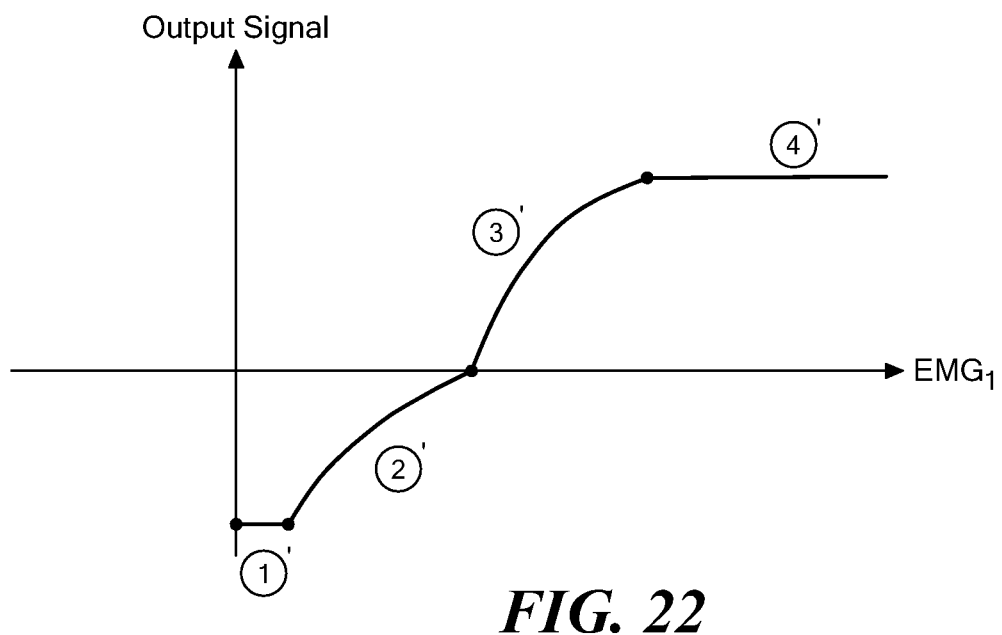
FIG. 22 shows a graph of EMG signal vs. output signal according to illustrative embodiments of the present invention.

FIG. 22 shows a graph depicting features of another control algorithm. In this scenario, there may be output signal saturation in the second direction (1'), as well as in the first direction (4'). FIG. 22 also depicts a non-linear relationship between EMG1 and output signal in both the first (2') and second (3') directions, with a break point coinciding with the zero-crossing.

Figure 23:
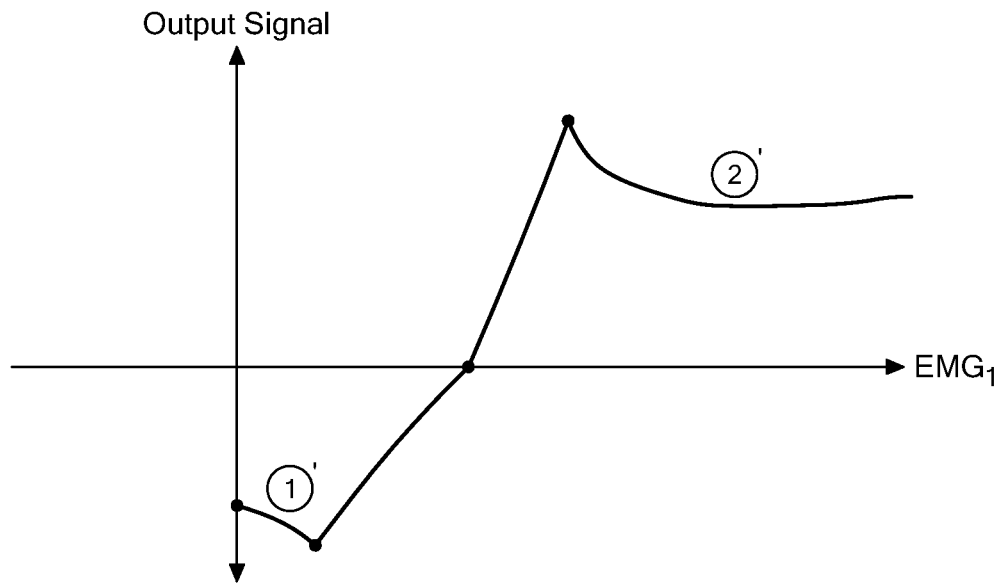
FIG. 23 shows a graph of EMG signal vs. output signal according to illustrative embodiments of the present invention.

FIG. 23 shows a graph depicting features of another control algorithm. As shown, the relationship between output signal and EMG1 is not necessarily monotonic, but may have inflection points, where the slope changes from decreasing to increasing (1'), or vice versa (2'). For example, the maximum absolute output signal value for each direction may be reached before the output signal saturates, or before EMG1 reaches zero.

Figure 24:
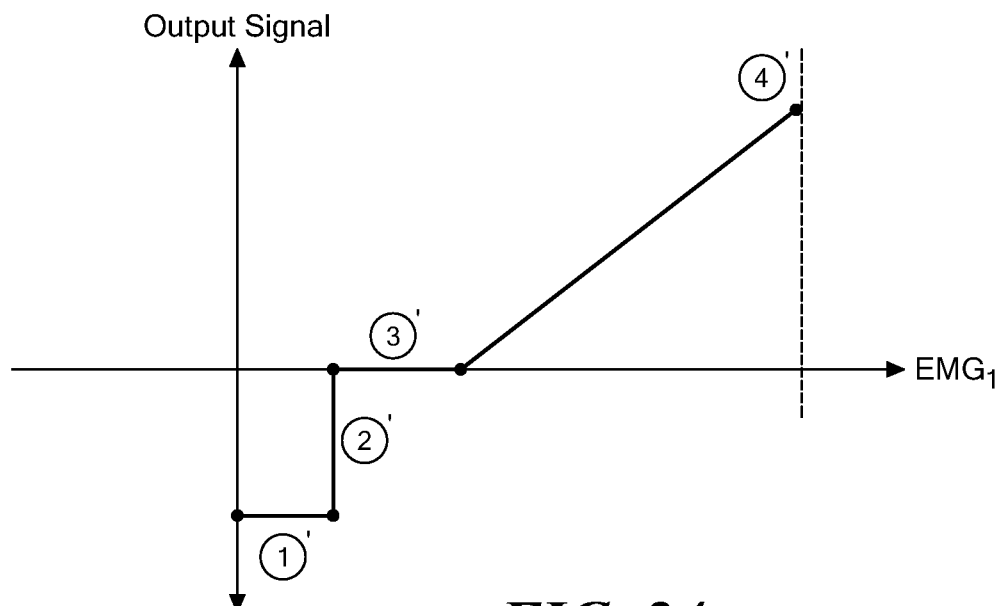
FIG. 24 shows a graph of EMG signal vs. output signal according to illustrative embodiments of the present invention.

FIG. 24 shows a graph depicting features of another control algorithm. As shown, there may be regions of zero slope (1'), regions of infinite slope (2'), or discontinuities (3') in the relationship between output signal and EMG1. For example, the output signal may be constant for low values of EMG1 and then the value may jump to zero at a certain value of EMG1. Also, the output signal may not change direction (and cause torque in the first direction) until the value of EMG1 reaches yet another, higher value. This may be thought of as a "dead band" (3'), which may act to minimize the sensitivity of the output signal to small perturbations in EMG1 about some nominal value.

Figure 25:
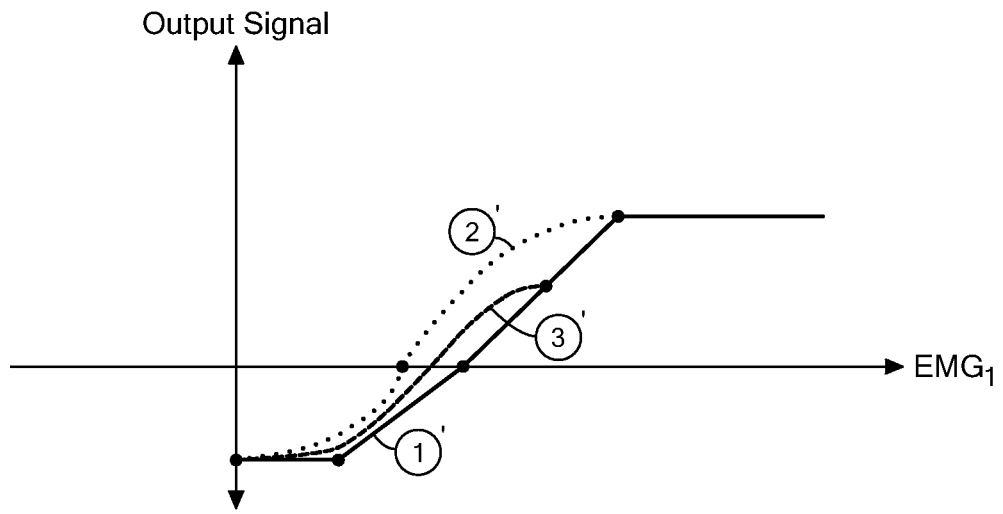
FIG. 25 shows a graph of EMG signal vs. output signal according to illustrative embodiments of the present invention.

FIG. 25 shows a graph depicting features of another control algorithm. As shown, there may be hysteresis in the relationship between output signal and EMG1. The relationship may follow a certain path if EMG1 is increasing, and may follow a different path if EMG1 is decreasing. For example, the output signal may follow curve (1') if EMG1 is increasing, and the output signal may follow curve (2') if EMG1 is decreasing. Alternatively, the output signal may follow a hysteretic path (3') which departs directly from the "EMG1 increasing" or "EMG1 decreasing" curve, when EMG1 changes direction (rather than making a discontinuous jump from one curve to another, as in (2')).

Figure 26:
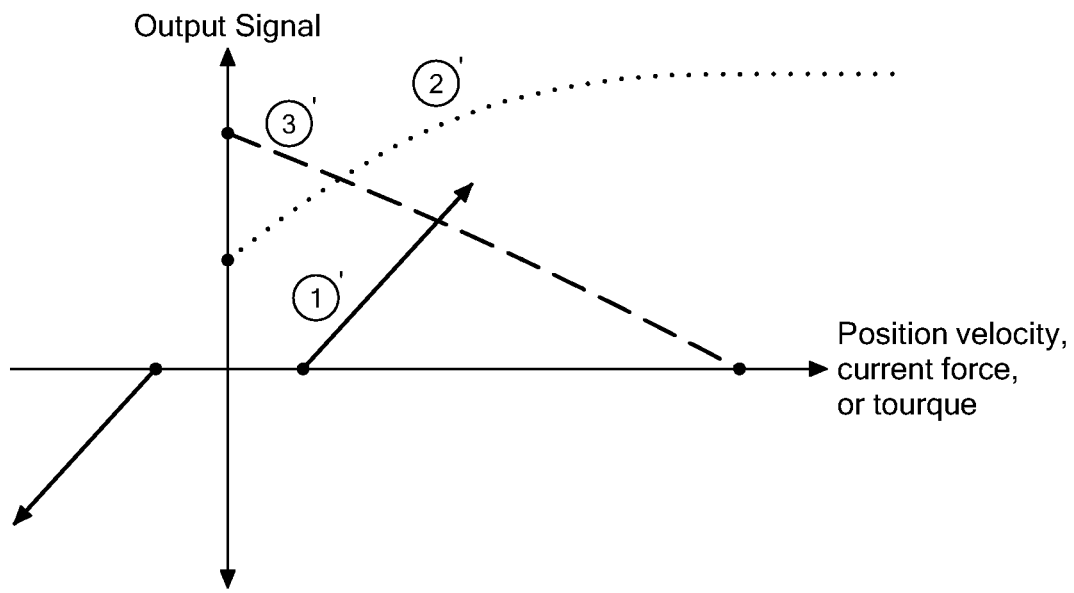
FIG. 26 shows a graph of other parameters vs. output signal according to illustrative embodiments of the present invention.

FIG. 26 shows a graph depicting features of another control algorithm, showing the potential relationship between a control output signal and other measured parameters such as joint position, joint velocity, current and various measured forces or torques. As shown, the relationships may be linear (1') or non-linear (2', 3'), increasing or decreasing (3') or both. The relationship may be continuous or discontinuous (1'), and may have positive and negative components. The relationship may also be asymptotic, and may have saturation limits (2').

Figure 27:
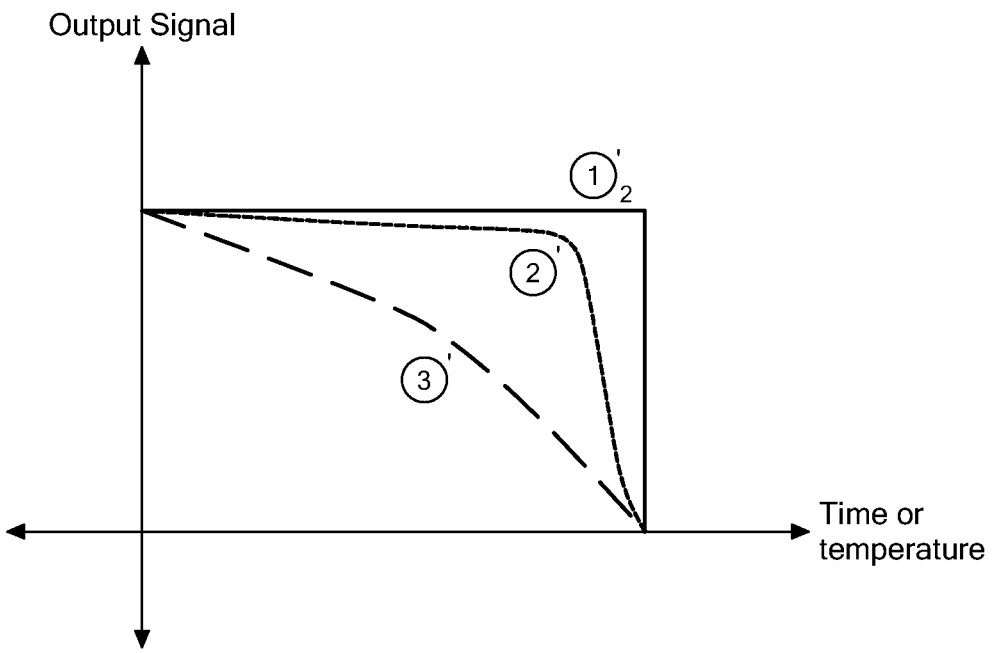
FIG. 27 shows a graph of time or temperature parameters vs. output signal according to illustrative embodiments of the present invention.

FIG. 27 shows a graph depicting features of another control algorithm, showing the potential relationship between a control output signal and other measured or unmeasured parameters such as temperature or time. As shown, the relationship may be linear or non-linear (1', 2', 3'), increasing or decreasing (3') or both. The relationship may be continuous or discontinuous (1'), and may have positive and negative components. The relationship may also be asymptotic, and may have saturation limits (2'). They may have regions of zero slope, and regions of infinite slope (1').

Figure 28:
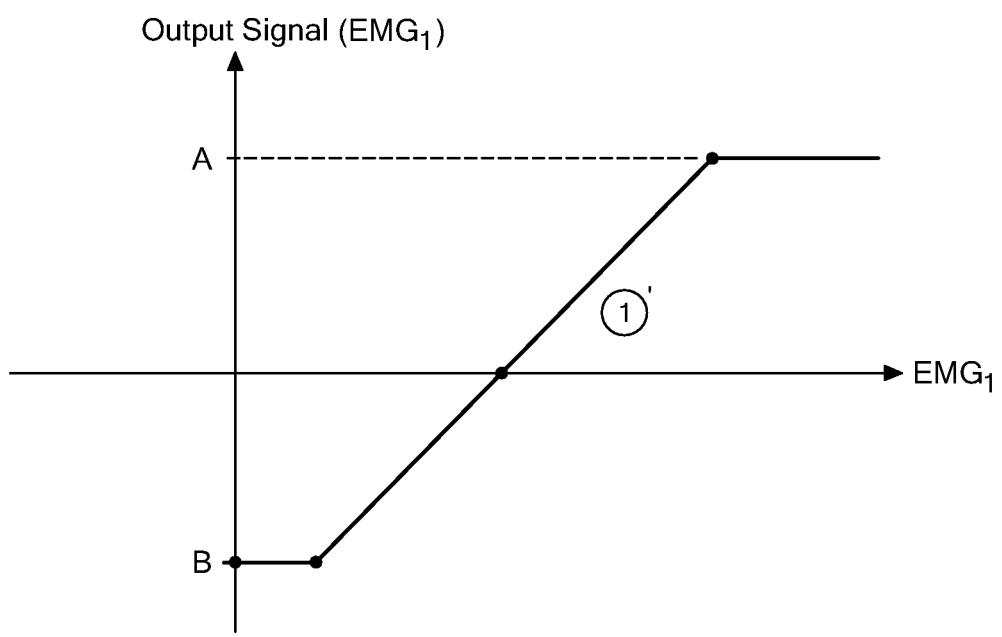
FIG. 28 shows a graph of EMG signal vs. output signal according to illustrative embodiments of the present invention.
Figure 29:
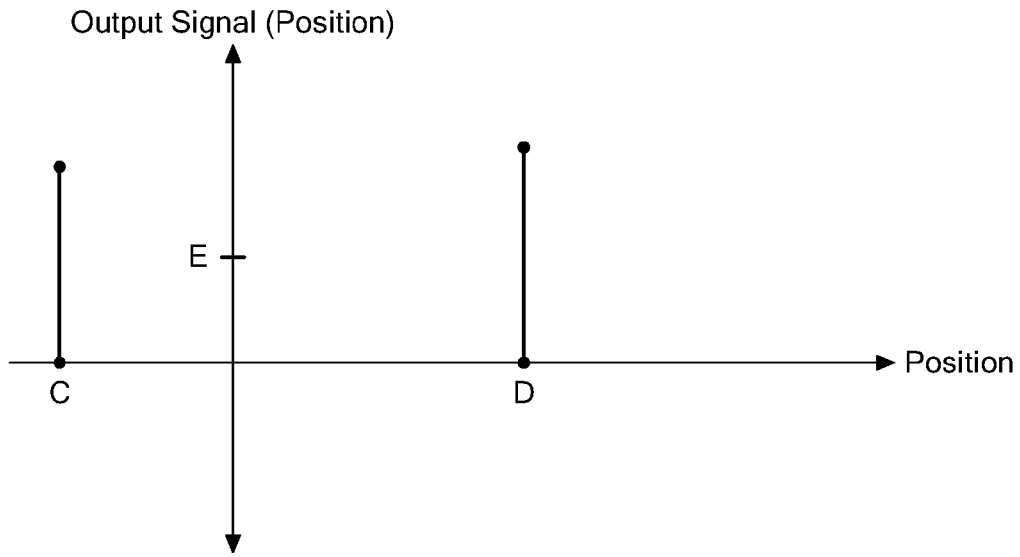
FIG. 29 shows a graph of position vs. output signal according to illustrative embodiments of the present invention.
Figure 30:
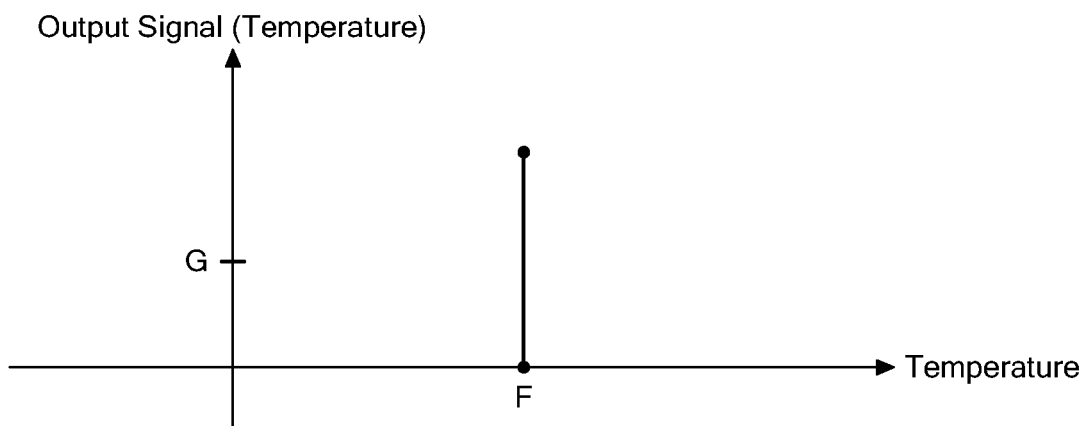
FIG. 30 shows a graph of temperature vs. output signal and a control algorithm according to illustrative embodiments of the present invention.

FIGS. 28-30 show graphs depicting features of an asymmetric control algorithm. The equation for the command output to the actuator assembly is shown in FIG. 30. As shown, the slope of the line (1'), and the values of the constants (A, B, C, D, E, F, G) are adjustable via the user interface.

EXAMPLES

Figure 31:
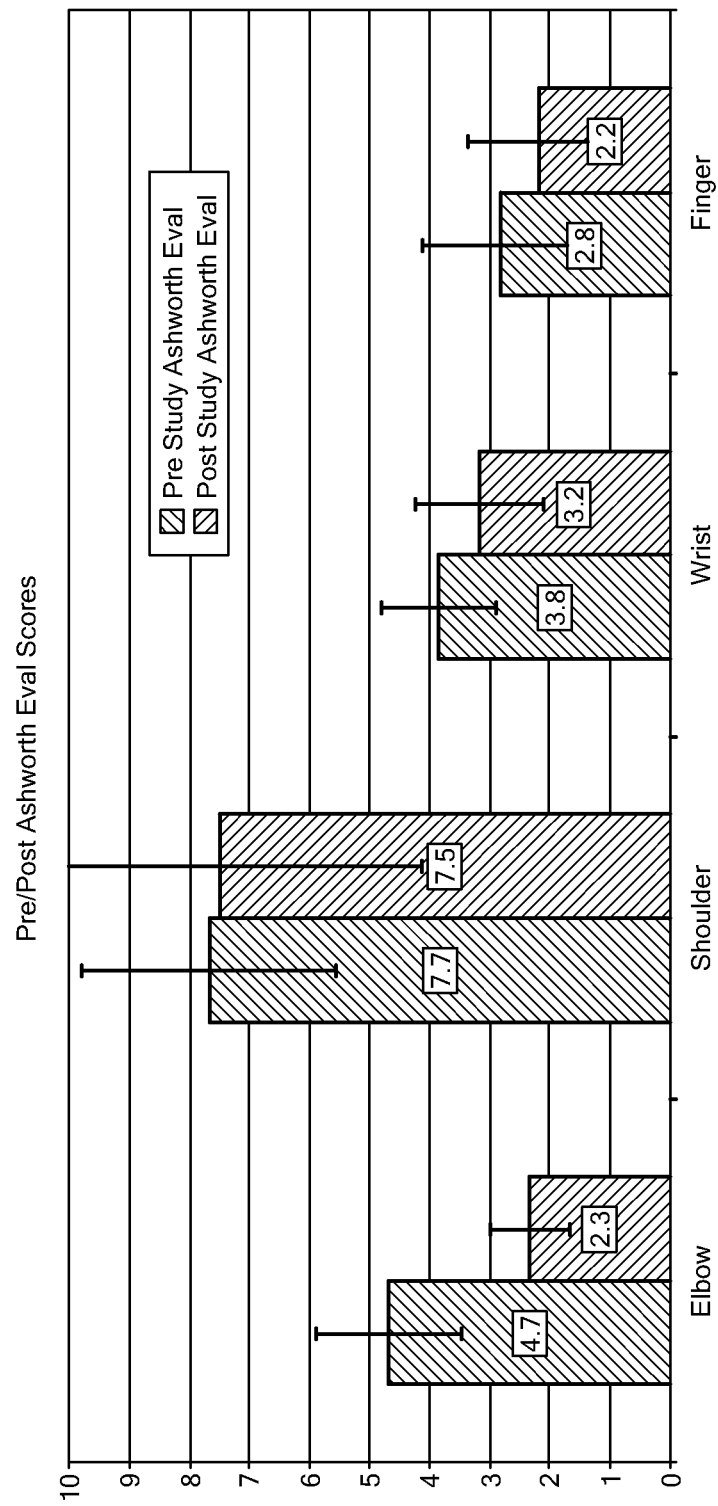
FIG. 31 shows pre and post Ashworth evaluation scores for users of an orthotic device according to illustrative embodiments of the present invention.
Figure 32:
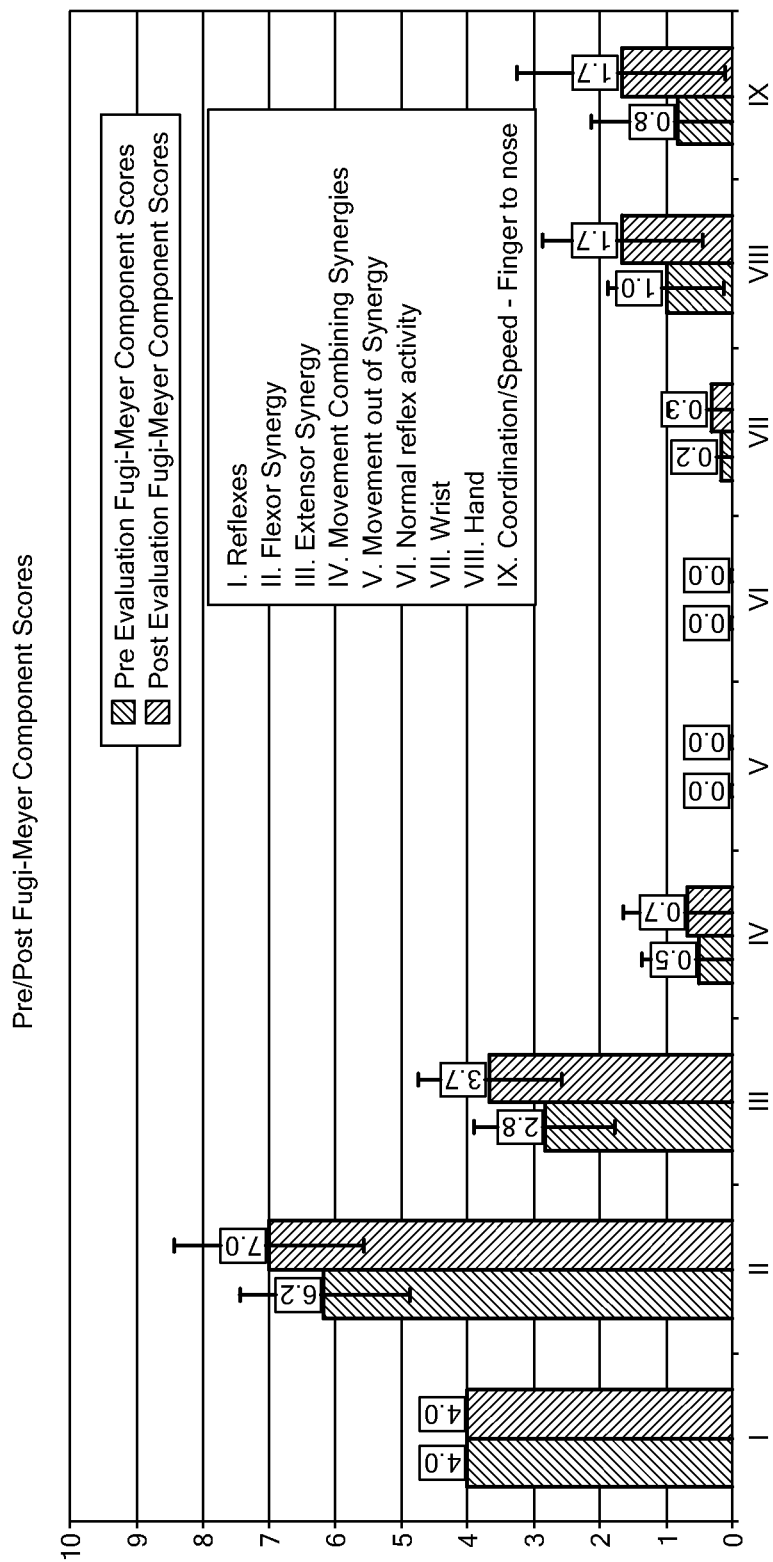
FIG. 32 shows pre-evaluation and post-evaluation Fugl-Meyer Component scores for users of an orthotic device according to illustrative embodiments of the present invention.

An asymmetric EMG-controlled orthotic device in accordance with embodiments described herein was built and used in clinical trials on healthy individuals and on stroke survivors. The control algorithms proved effective in both enabling stroke survivors to control the device, and in promoting rehabilitation of the afflicted joint(s). FIGS. 31 and 32 are graphs showing rehabilitation progress of the subjects in the clinical trial, according to industry-standard rehabilitation scales (Fugl-Meyer and Ashworth).

Embodiments of an EMG-controlled orthotic device may be used in a variety of ways and with various protocols as a rehabilitation or functional aid. For example, rehabilitative exercise regimes may include the execution of familiar and/or functional tasks, or components thereof, to enhance the user's functional capacity. To this end, a subject's functional capabilities may be first assessed and classified into various levels without the device on. For example, three levels of classification that may be used are listed below, although any number of levels having various characteristics may be employed. In addition, although the levels of classification are related to arm motion and related therapies, levels with other characteristics may be used for other parts of the body, e.g., leg, hand/wrist, or foot/ankle. The examples below are thus exemplary.

Level III: skilled movement
  Goal: use arm to successfully perform functional tasks, integrating all components
  Characteristics:
    volitional motion of arm, out of synergies
    no extra proprioceptive input required to perform motion
    able to consistently have volitional alternating flex/extension to perform functional activity
    verbal cues to minimal assistance to block abnormal shoulder motions
    none or verbal cues for posture required
    can perform tasks with better speed, smoothness of alternating from flexion to extension
    increased frequency and endurance in therapy
    low assistance required during therapy
    can perform tasks in multiple planes and diagonals, with functional mobility, and increased challenges to task
Level II: increased controlled motion relative to Level I
  Goal: move joints in available range of flexion and extension to perform functional task components
  Characteristics:
    consistent volitional motion of bicep and tricep
    requires some extra proprioceptive input to perform motion
    mixed use of synergies
    minimal to moderate assistance required to block abnormal shoulder motion
    moderate verbal cues required for posture
    can perform tasks slowly, may be 'jerky'
    moderate endurance in therapy, can tolerate some increased frequency and repetition of tasks
    moderate assistance required during therapy
    can perform tasks best in straight planes, seated or standing
Level 1: stability and mobility
  Goals: achieving maximal active range of motion and providing a stable base for movement
  Characteristics:
    some EMG reading of the bicep and/or tricep
    requires extra proprioceptive input to perform motion, may require manual pronation/supination by therapist
    little volitional motion of arm out of synergies
    unable to consistently fire muscles to perform functional activity
    requires moderate to maximal assistance to block abnormal shoulder motion
    requires maximal verbal cues for posture
    high level of assistance required during therapy
    most tasks performed seated or as easiest For example, a subject with very limited capability may have one or more characteristics falling within Level I, a subject with limited capability may have one or more characteristics falling within Level II, and a subject with a more moderate capability may have one or more characteristics falling within Level III. Of course, a subject may have one or more characteristics falling within two levels when the subject's capability is transitioning from one level to the next, e.g., between Level I and Level II or between Level II and Level III.

After assessing the subject's capability without a device in accordance with embodiments herein, various physical tasks may be performed while using or wearing the device. While using the device, the subject typically has characteristics falling within the subject's assessed capability level and may have some characteristics falling within a higher level. For example, if a subject is assessed at Level I without using the device, then the subject may have characteristics falling within Level I and Level II when using the device. The physical tasks may include different categories or types of movements that utilize various aspects of the affected muscles. For example, the physical tasks may include the following categories for a subject with impaired arm functionality:

A. utilize gross bilateral grip to manipulate an object in a functional setting
B. utilize the affected arm to increase volitional unilateral extension for a functional task
C. utilize the affected arm to stabilize an object in order to perform a functional task with the unaffected arm
D. increase volitional unilateral flexion and release for a functional task Some of the physical tasks that may be utilized for each category and level are listed below. Under some of the physical tasks, the a and b subheadings may include different adaptations of the same task or ways to modify the task to increase/decrease the difficulty of the task.

Category A, Level 3. Bilateral reach, lift, and carry laundry basket/box/crate
  a. add functional mobility
  b. increase weight or size of object used in task
Category A, Level 3. Bilateral reach, manipulate and stack boxes on table
  a. utilize different planes, diagonals, or surface heights
Category A, Level 2. Lift box straight up on table at mid line, bilateral grip
  a. increase repetitions and speed performed
  b. increase weight or size of object used
Category A, Level 2. Push and pull crate or box on table
  a. increase weight or size of object used
Category A, Level 2. Push-pull task with wooden staff or using rolling pin
  a. increase speed in which exercise is performed
  b. standing, leaning back on wall
Category A, Level 2. Modified push up on wall/rhythmic stabilization
  a. increase repetitions and speed performed
Category A, Level 2. Bilateral rowing task with wooden staff (repetitive-bilateral exercise)
  a. increase speed
  b. increase use of shoulder flexion Category A, Level 2. Bilateral use of arm for towel or clothing folding task Category A, Level 2. Copy similar motions performed simultaneously by the contralateral arm.

Category A, Level 2. Hold ball with bilateral grip at mid line, flex and extend
  a. focus task on motions outside of synergistic patterns
  b. increase repetitions performed Category A, Level 1. Hold ball with bilateral grip at mid line
  a. increase amount of time spent to hold static position Category A, Level 1. Weight bearing through affected arm
  a. increase amount of time spent to hold static position
  b. use EMG reading to assess muscle firing Category B, Level 3. Unilateral reach to open doorknob with affected arm (same sequence for light switch or drawer)
  a. utilize different planes, diagonals,
  b. increase speed Category B, Level 3. Unilateral reach to moving target such as balloon
  a. utilize different planes, diagonals, or surface heights
  b. arm resting on large physioball on table to assist with gravity Category B, Level 2. Unilateral reach to a static target on table
  a. utilize different planes, diagonals, or surface heights
  b. focus task on motions outside of synergistic patterns Category B, Level 2. Tricep facilitated sit to stand Category B, Level 1. Unilateral seated bicep curls or tricep extension
  a. focus on partial ranges
  b. closed chain into ball Category B, Level 1. Volitional firing of tricep muscle Category B, Level 1. Weight bearing through affected arm
  a. increase amount of time spent to hold static position
  b. use EMG reading to assess muscle firing Category C, Level 3. Carrying household items with affected arm
  a. utilize different planes, diagonals, or surface heights
  b. reach to pick up jar then stabilize to open
  c. increase weight or size of object Category C, Level 3. Stabilize jar with affected arm to open
  a. add functional mobility
  b. increase weight or size of object Category C, Level 2. Stabilize household item with affected arm flexed 90 degrees
  a. increase weight or size of object Category C, Level 1. Hold jar or ball with affected arm, hold for longer periods of time
  a. increase weight or size of object used Category C, Level 1. Hold paper on table with affected arm in order to write
  a. increase amount of time spent to hold static position
  b. use EMG reading to assess muscle firing Category D, Level 3. Drinking from a cup (adapted as needed)

Category D, Level 3. Reach to face to shave or reach with hairbrush

Category D, Level 2. Wipe mouth with napkin

Category D, Level 2. Flex arm towards mouth from lap
  a. use EMG reading to assess muscle firing Category D, Level 1. Unilateral seated bicep curls or tricep extension
  a. focus on partial ranges Category D, Level 1. Volitional firing of bicep muscle
  a. focus on motions outside of synergistic patterns
  b. use EMG reading to assess muscle firing Thus, a subject's rehabilitation therapy using embodiments of the device may include one or more physical tasks that fall within these different categories within the subject's assessed level of capability or a higher level. For example, a subject classified at Level 1 without using the device, may attempt to perform one or more of the Category A, B, C and/or D, Level 1 tasks or Category A, B, C and/or D, Level 2 tasks while using the device.

When the subject performs these physical tasks, various metrics may be observed and/or recorded in accordance with embodiments of the present invention. For example, the amount of assistance needed from the device during flexion/extension, the number of repetitions achieved and time required to perform them, amount of physical or motivational assistance required (e.g., verbal cues, minimal, moderate, maximal), and/or quality of motion (e.g., jerky, smooth).

The following is an example of a therapy session:

During the Session

Record which number session for the person

Ask the person:

Any changes in health or medications?

Any changes in the use of your arm at home?

Record subjective quotes

Perform basic warm-up (e.g., about 10 minutes). This may include the following:
  roll shoulders both directions
  shoulder retraction, hold, relax
  neck stretches
  elbow: Passive Range of Motion (PROM), Active Assisted Range of Motion (AAROM), stretching as applicable.

The warm-up time may be used to assess patient tone or which muscles to start with (e.g., bicep/tricep)

Start session in bicep mode—don brace and assess if calibrated well (e.g., 2-5 minutes)

Chose activities by classification level of subject (e.g., 15-20 minutes). This may include the following:
  perform muscle specific activity, e.g., seated bicep curl in isolated ranges
  perform functional components, e.g., have subject try to flex arm and actively relax back down to lap
  attempt functional task to abilities of subject, e.g., put adapted cup with straw in subject's hand and have them bring the cup to mouth Change to tricep mode and assess if calibrated well (e.g., 2-5 minutes)

Chose activities by classification level of subject (e.g., 15-20 minutes). This may include the following:
  perform muscle specific activity, e.g., seated tricep extension in isolated ranges
  perform functional components, e.g., have subject isometric extension and relax onto ball or leg
  attempt functional task to abilities of subject, e.g., attempt tricep facilitated sit-stand Record all activities in a written report as they are occurring. For example, the report may include the following:
  performed tricep facilitated sit to stand; start time: 10:30 AM stop time: 10:35 AM total time: 00:05 min. Assistance in one direction (gain): 8; assistance in other direction (spring): 2
  moderate physical assistance, able to attempt 5 times with smooth motions In the reports, may use the category "recalibrate to tricep mode" or "set up and calibrate" and specify whether using brace in bicep or tricep mode.

Summarize the Session

Record subjective quotes, record time spent performing each task

Rate the overall assessment of subject's performance. This may be in the form of a checklist.

Note any general recommendations for the next session, e.g., attempt more activities in tricep mode, focus on increasing speed of performance, note techniques that worked/did not work well with the person.

The following may be performed once a week during one of the therapy sessions:

Measure Active Range of Motion (AROM), PROM of elbow flexion/extension pre and post session.

Note changes in sensation reported by subject

Have subject touch hand from left knee to nose 5 times. Record time (and distance if not able to touch nose or chin)

Perform modified Ashworth assessment of arm and hand tone using the following rating system:

0 No increase in muscle tone

1 Slight increase in muscle tone, manifested by a catch and release or by minimal resistance at the end of the range of motion when the affected part(s) is moved in flexion or extension 2 Slight increase in muscle tone, manifested by a catch, followed by minimal resistance throughout the reminder (less than half) of the ROM (range of movement)

3 More marked increase in muscle tone through most of the ROM, but affected part(s) easily moved 4 Considerable increase in muscle tone passive, movement difficult 5 Affected part(s) rigid in flexion or extension Embodiments of an EMG-controlled orthotic device may be used in a variety of ways during a rehabilitation or therapy session or while performing one or more physical tasks. For example, the level of assistance provided by the device may be modified in one or both directions during the execution of a task or repetition (e.g., if certain components of the task are more difficult than others), during the execution of a series of tasks or repetitions, over the course of a therapy session or routine (e.g., as the subject may 'warm up' or fatigue over the course of the session), and/or over a period of time spanned by several therapy sessions, as the subject's level of functionality (and consequent need for assistance) may increase or decrease over such time. For instance, if the subject is having difficulty moving the arm in flexion, but only at the beginning of the motion, then the device may provide additional assistance at first and then provide less assistance during the remainder of the range of motion so that the subject uses his or her muscles more than would otherwise be permitted. If the subject becomes fatigued or tires during the course of a task or series of tasks, then the device may provide increased amounts of assistance over time so that the subject may continue to use the muscles, allowing additional movement training or exercise (e.g., conditioning of the muscles) and increasing the subject's endurance level beyond that which would otherwise be permitted. If the subject's conditioning improves over the course of the therapy or series of tasks, then the device may provide less assistance over time or may increase the level of resistance so that the subject uses his or her muscles more than would otherwise be permitted. If the subject has difficulty in one motion direction, e.g., flexion, but not the other, e.g., extension, then the device may provide additional assistance in one direction compared to the other direction. The increased or decreased amount of assistance provided by the device may be adjusted automatically by the device and/or manually by the user and/or trained individual. The device may be used to temporarily increase the stiffness of a subject's limb, to allow body weight support, body stabilization, or the stabilization of objects in bi-manual tasks (for example, holding a large jar with the affected limb wearing the device, while unscrewing the lid with the unaffected hand/arm).

Adjusting the assistance level of an EMG-controlled orthotic device in accordance with an embodiment of the present invention may improve the quality of motion of a subject's affected limb, by increasing the smoothness, speed, accuracy and strength of its motion. When the device is worn on the affected arm, and physical tasks are performed that require use of both hands or arms, the device may allow the unaffected arm to guide the affected arm through a trajectory to achieve a goal, or may allow the affected arm to achieve the gross motor components of a task (e.g., stabilizing a body or object, holding an object in place, providing a surface against which to push, moving a hand or object through gross trajectories), while the unaffected arm performs the higher dexterity functions (e.g., operations that require dexterous finger motions, finer manipulation of objects, tying shoes, unscrewing lids, grasping objects or handles).

An EMG-controlled orthotic device in accordance with a further embodiment of the present invention may provide feedback to a clinician or user during use, e.g., tactile, visual, audio, or other sensory feedback. For example, during a task or a series of tasks, the clinician or user may visually observe the muscle activity occurring through the display 20 on the user interface. The user interface may also provide verbal encouragement and/or visual goals for the user during its use. Visually displaying the EMG activity of one or more of the subject's muscles may heighten the subject's awareness of any unintentional muscle activity, allowing the subject to pay closer attention to the states of the muscles, and to consequently remain focused on the states of the muscles. Thus, the device may train a subject to relax a muscle that may be tight, or may be firing unintentionally (e.g., as a result of high tone, synergistic motion patterns, or lack of inhibitory signals from the brain) when the subject focuses on relaxing the affected muscles that control motion about the joint while the device applies torque to move the limb in a direction that stretches the muscle that is tight or is firing unintentionally.

Although various exemplary embodiments of the invention have been disclosed, it should be apparent to those skilled in the art that various changes and modifications can be made which will achieve some of the advantages of the invention without departing from the true scope of the invention.

What is claimed is:

1. A powered orthotic device comprising:
   a brace having a first section and a second section, the first section and the second section operationally coupled at a pivot, the first and the second sections moving about the pivot to define flexion and extension directions, such directions defining inside and outside regions of the brace respectively, the brace configured to removably attach the first section and the second section to a corresponding limb segment such that the pivot is proximate to a joint between each limb segment;
   an electromyographic sensor; and
   an electrically powered actuator assembly in communication with the electromyographic sensor, the actuator assembly mounted to the brace, and occupying a volume of which a majority is disposed proximately to the outside region of the brace, and coupled to the first and the second sections of the brace so as to apply a force for driving the first and second sections about the pivot, the force based on signals from the electromyographic sensor, wherein the actuator assembly includes a motor in a housing and a drive assembly coupled to the motor and coupled to the first and second sections of the brace, the housing disposed proximate to the pivot and coupled to the brace at the pivot, and having a longitudinal axis that is parallel to, and non-coaxial with, an axis of rotation of the joint and the drive assembly disposed in a plane substantially perpendicular to the longitudinal axis of the housing;

so that the brace and the actuator assembly form a wearable component.

2. A device of claim 1, wherein the motor is disposed proximately to the outside region of the brace.

3. A device of claim 1, further comprising a control system in communication with the electromyographic sensor and with the motor for controlling operating parameters of the device.

4. A device of claim 3, wherein the control system is in communication with the electromyographic sensor and the motor via a cable.

5. A device of claim 3, wherein the control system is in communication with the electromyographic sensor and the motor through a wireless system.

6. A device of claim 3, wherein the control system includes a user interface through which a user interacts with the device.

7. A device of claim 3, wherein the control system includes a processing system for receiving the signals from the electromyographic sensor and generating output signals to the motor.

8. A device of claim 7, wherein the processing system includes software for limiting a range of motion of the sections about the joint.

9. A device of claim 3, wherein the control system includes a data management system for storing data received from the device, from a user or both.

10. A device of claim 1, further comprising a user interface, in communication with the electromyographic sensor and the motor, through which a user interacts with the device.

11. A device of claim 1, further comprising a processing system, in communication with the electromyographic sensor and the motor, for receiving the signals from the electromyographic sensor and generating output signals to the motor.

12. A device of claim 11, wherein the processing system includes a data management system for storing data received from the device, from a user or both.

13. A device of claim 1, further comprising motion limits coupled to the drive assembly for limiting a range of motion of the sections about the joint.

14. A device of claim 13, wherein the motion limits are provided by mechanical stops, by sensors, or both.

15. A device of claim 1, further comprising a planetary gear head coupled to the motor and to the drive assembly.

16. A device of claim 1, wherein the drive assembly includes a chain and sprocket.

17. A device of claim 1, wherein the brace further includes at least one pad coupled to the first section, the second section, the pivot, or a combination thereof.

18. A device of claim 1, wherein the brace is removably attached to an arm and the pivot is proximate to an elbow.

19. A device of claim 1, wherein the brace is removably attached to an arm and a hand and the pivot is proximate to a wrist.

20. A device of claim 1, wherein the brace is removably attached to a hand and at least one finger and the pivot is proximate to a finger joint.

21. A device of claim 1, wherein the electromyographic sensor is coupled to at least one of the straps, to at least one of the sections, to a padding coupled to at least one of the sections, or a combination thereof.

22. A powered orthotic device comprising:

a brace having a first section and a second section, the first section and the second section operationally coupled at a pivot, the first and the second sections moving about the pivot to define flexion and extension directions, the brace configured to removably attach the first section and the second section to a corresponding limb segment such that the pivot is proximate to a joint between each limb segment;

an electromyographic sensor;

an actuator assembly in communication with the electromyographic sensor, the actuator assembly mounted to the brace and coupled to the first and the second sections of the brace so as to apply a force for driving the first and second sections about the pivot, the force based on signals from the electromyographic sensor, wherein the actuator assembly includes a motor in a housing and a drive assembly coupled to the motor and coupled to the first and second sections of the brace, the housing disposed proximate to the pivot and coupled to the brace at the pivot, and having a longitudinal axis that is parallel to, and non-coaxial with, an axis of rotation of the joint and the drive assembly disposed in a plane substantially perpendicular to the longitudinal axis of the housing, so that the brace and the actuator assembly form a wearable component;

a controller coupled to the actuator assembly that controls operation of the actuator assembly; and a user interface, coupled to the controller, that permits user adjustment of force parameters of the actuator assembly.

23. A device of claim 22, wherein the user interface permits user adjustment of assistance levels in the flexion direction and the extension direction independently of one another.

24. A device of claim 22, wherein the user interface permits user adjustment of assistance levels while the device is in use.

25. A powered orthotic device comprising:

a brace having a first section and a second section, the first section and the second section operationally coupled at a pivot, the brace configured to removably attach the first section and the second section to a corresponding limb segment such that the pivot is proximate to a joint between each limb segment;

an electromyographic sensor;

an actuator assembly in communication with the electromyographic sensor, the actuator assembly mounted to the brace and coupled to the first and the second sections of the brace so as to apply a force for driving the first and second sections about the pivot, the force based on signals from the electromyographic sensor, wherein the actuator assembly includes a motor in a housing and a drive assembly coupled to the motor and coupled to the first and second sections of the brace, the housing disposed proximate to the pivot and coupled to the brace at the pivot, and having a longitudinal axis that is parallel to, and non-coaxial with, an axis of rotation of the joint and the drive assembly disposed in a plane substantially perpendicular to the longitudinal axis of the housing, so that the brace and the actuator assembly form a wearable component;

a controller coupled to the actuator assembly that controls operation of the actuator assembly; and a user interface, coupled to the controller, that permits user selection of operational mode of the device from among at least two of high assist, low assist, resistive, therapeutic training, and functional assistive.

26. A device of claim 25, wherein the user interface permits a user selection of operational mode from among at least three of high assist, low assist, resistive, therapeutic training, and functional assistive.

27. A powered orthotic device for use by a user having a pair of limb segments movable with respect to a joint, the device comprising:
- a brace having a first section and a second section, the sections operationally coupled to each other at a pivot, each section corresponding to one of the pair of limb segments, the sections moving with respect to each other to define flexion and extension directions, the brace configured to removably attach at least one of the sections to its corresponding limb segment of the joint;
- a control system;
- an electromyographic sensor coupled to the control system;
- an actuator assembly coupled to the control system so as to apply a force driving the first and second sections in at least one of the flexion and extension directions, the force based on signals from the electromyographic sensor, wherein the actuator assembly includes a motor in a housing and a drive assembly coupled to the motor and coupled to the first and second sections of the brace, the housing disposed proximate to the pivot and coupled to the brace at the pivot, and having a longitudinal axis that is parallel to, and non-coaxial with, an axis of rotation of the joint and the drive assembly disposed in a plane substantially perpendicular to the longitudinal axis of the housing, so that the brace and the actuator assembly form a wearable component; and
- a user interface coupled to the control system, such interface accessible to and operable by the user in the course of operation of the device, by which the user may adjust at least one parameter affecting operation of the device.

28. A device according to claim 27, wherein the user interface is wearable on the user's body.

29. A device according to claim 27, wherein the user interface is located on the brace.

30. A device according to claim 27, wherein the user interface is located on the control system.

31. A device according to claim 27, wherein the user interface comprises one or more of a knob, button, switch, touch sensor, display screen, touch screen, audio device, visual alarm, tactile transmitter, port for external connection.

32. A device according to claim 27, wherein the user interface includes at least one of knobs and levers for receiving mechanical input from the user.

33. A device according to claim 27, wherein the user interface provides at least one of tactile, visual, and audio feedback to the user.

34. A device according to claim 27, wherein the interface includes a display that reports usage data.

35. A device according to claim 34, wherein usage data include at least one of range of motion, number of repetitions, velocity, torque, force, position, rehabilitation progress, number of exercises completed, elapsed time, EMG amplitude, EMG activity, device settings.

36. A device according to claim 27, wherein the user interface is coupled to the control system by a wireless connection.

37. A device according to claim 27, wherein the control system may be coupled to the Internet, so that the device may communicate with a clinician remotely located.

38. A device according to claim 27, wherein the user interface permits adjustment of at least two of brace strength, system gains, system sensitivities, virtual spring parameters, EMG threshold values, maximum and minimum torques, operational range of motion, damping parameters, user feedback modes, and data logging parameters.

39. A device according to 27, wherein the at least one parameter includes at least one of level of assistance and level of resistance in at least one of flexion direction and extension direction.

40. A device according to claim 27, wherein the interface permits user selection of operational mode of the device.

41. A device according to claim 40, wherein the interface permits user selection of operational mode from among at least two of high assist, low assist, resistive, therapeutic training, functional assistive, bicep, tricep, passive, responsive, facilitation, and training session.

42. A device according to claim 27, wherein the user interface permits uploading of user profiles pertinent to operation of the device.

43. A device according to claim 27, wherein the user interface includes access control that restricts adjustment of selected parameters to individuals satisfying access criteria.

44. A device according to claim 27, wherein the user interface permits parameters affecting device operation in the flexion direction and parameters affecting device operation in the extension direction to be adjusted by the user independently of one another.

* * * * *